United States Patent
Schinazi et al.

(10) Patent No.: US 6,583,122 B2
(45) Date of Patent: Jun. 24, 2003

(54) NUCLEOSIDES AND OLIGONUCLEOTIDES CONTAINING BORON CLUSTERS

(75) Inventors: Raymond F. Schinazi, Decatur, GA (US); Geraldiné Fulcrand-El Kattan, Atlanta, GA (US); Zbigniew Jan Lesnikowski, Decatur, GA (US)

(73) Assignee: Emory University, Atlanta, GA (US)

(*) Notice: Subject to any disclaimer, the term of this patent is extended or adjusted under 35 U.S.C. 154(b) by 12 days.

(21) Appl. No.: 09/774,223

(22) Filed: Jan. 30, 2001

(65) Prior Publication Data

US 2002/0160969 A1 Oct. 31, 2002

Related U.S. Application Data

(62) Division of application No. 08/161,674, filed on Dec. 2, 1993, now Pat. No. 6,180,766.

(51) Int. Cl.[7] .................. A01N 43/04; C07H 21/00; C07H 21/04; C12Q 1/68
(52) U.S. Cl. .............. 514/44; 536/22.1; 536/25.3; 536/25.32; 435/6
(58) Field of Search ............. 536/22.1, 25.3, 536/25.32; 435/6; 514/44

(56) References Cited

U.S. PATENT DOCUMENTS

| | | |
|---|---|---|
| 4,516,535 A | 5/1985 | Russell, Jr. et al. |
| 4,522,811 A | 6/1985 | Eppstein et al. |
| 4,855,493 A | 8/1989 | Spielvogel et al. |
| 4,959,356 A | 9/1990 | Miura et al. |
| 5,021,572 A | 6/1991 | Gabel |
| 5,066,479 A | 11/1991 | Hawthorne |
| 5,130,302 A | 7/1992 | Speilvogel et al. |
| 5,171,849 A | 12/1992 | Soloway et al. |
| 5,272,250 A | 12/1993 | Spielvogel et al. |
| 5,328,678 A | 7/1994 | Fujii et al. |
| 5,405,598 A | 4/1995 | Schinazi et al. |
| 5,466,679 A | 11/1995 | Soloway et al. |
| 5,599,796 A | 2/1997 | Schinazi et al. |
| 5,872,107 A | 2/1999 | Schinazi et al. |

FOREIGN PATENT DOCUMENTS

| | | |
|---|---|---|
| EP | 0731808 B1 | 7/2001 |
| JP | 5163296 | 6/1993 |
| WO | WO91/08213 | 6/1991 |
| WO | WO91/09048 | 6/1991 |
| WO | WO93/17028 | 9/1993 |
| WO | WO95/15333 | 6/1995 |
| WO | WO95/26359 | 10/1995 |
| WO | WO96/14073 | 5/1996 |

OTHER PUBLICATIONS

Andrus and Beaucage, "2–Mercaptobenzothiazole—Improved Reagent for the Removal of Methylphosphate Protecting Groups from Oligodexynucleotide Phosphotriesters," *Tetrahedron Letters*, (1988) 29:43, pp. 5479–5482.

Barth, et al., "Boron Neutron Capture Therapy of Cancer," *Cancer Research*, (1990) 50:1061–1070.

Barth, et al., "Boron Neutron Capture Therapy," *CANCER*, (1992) 70:12, pp. 2995–3007.

Baumgart, et al., "Site–specific mutagenesis induced by single $O^6$–alkylguanines ($O^6$.–n–propyl, $O^6$.–n–butyl, $O^6$.–n–octyl) in vivo," *Nucleic Acids Research*, (1993) 21:16, pp. 3755–3760.

Chen et al., "Synthesis and Characterization of Oligomeric nido–Carboranyl Phosphate Diester Conjugates to Antibody Fragments for Potential Use in Boron Neutron Capture Therapy of Solid Tumors," *Bioconjugate Chemistry*, (1994) 5:6, pp. 557–564.

(List continued on next page.)

*Primary Examiner*—Jezia Riley
(74) *Attorney, Agent, or Firm*—Sherry M. Knowles, Esq.; King & Spalding LLP

(57) ABSTRACT

Carboranyl-containing nucleosides and oligonucleotides are provided for use in boron neutron capture therapy (BNCT) and for other therapeutic and diagnostic purposes.

4 Claims, 7 Drawing Sheets

OTHER PUBLICATIONS

Cotton et al., Advanced Inorganic Chemistry, 4th Edition, *John Wiley & Sons*, (1980), pp. 318–320.

Fairchild, et al., "In Vitro Determination of Uptake, Retention, Distribution, Biological Efficacy, and Toxicity of Boronated Compounds for Neutron Capture Therapy: A Comparison of Porphyrins with Sulfhydryl Boron Hydrides," *Cancer Research*, (1990) 50, pp. 4860–4865.

Fairchild, et al., "Boron–10 Analysis by Prompt–Gama and Track–Etching Techniques" *Proc. The First International Symposium on Neutron Capture Therapy*, (Oct. 12–14, 1983), pp. 106–113.

Fujimori et al., "A Convenient and Steroselective Synthesis of 2'–Deoxy–β–L–Ribonucleosides," *Nucleosides & Nucleotides*, (1992) 11:2–4, pp. 341–349 (1992).

Fulcrand–El Kattan, et al., "Carboranyl Oligonucleotides. 2. Synthesis and Physicochemical Properties of Dodecathymidylate Containing 5–(o–Carboran–1–yl)–2'deoxyuridine," *J. Am. Chem. Soc.*, (1994) 116, pp. 7494–7501.

Fulcrand–el Kattan, Geraldine et al. "Synthesis and Biological Properties of 5–o–Carboranyl–1–(2–deoxy–2–fluoro–β–D–arabinofuranysyl) uracil," *J. Med. Chem.* (1994) 37:16, pp. 2583–2588.

Gabel, et al., "Determination of sub–PPM amounts of boron in solutions by means of solid state tract detectors," *Phys. Med. Biol.*, (1983) 28:12, pp. 1453–1457.

Gamper, et al., "Facile preparation of nuclease resistant 3' modified oligodeoxynucleotides," *Nucleic Acids. Research*, (1993) 21:1, pp. 145–150.

Genu–Dellac, C., et al., "3–substituted thymine –α–L–nucleoside derivatives as potential antiviral agents: synthesis and biological evaluation," *Antiviral Chem. & Chemo.*, (1991) 2:2, pp. 83–92.

Goudgaon, et al., "Boron Containing Pyrimidines, Nucleosides, and Oligonucleotides for Neutron Capture Therapy," *Nucleosides & Nucleotides*, (1994) 13:1–3, pp. 849–880.

Hatanaka and Sano, "A Revised Boron–Neutron Capture Therapy for Malignant Brain Tumours," *Z. Neurol.*, (1973) 204, pp. 309–332.

Hawthorne, "The Role of Chemistry in Development of Boron Neutron Capture Therapy of Cancer," *Angew, Chem. Int. Ed. Engl.* (1993) 32, pp. 950–984.

Heying, T. L. et al., "A new series of organoboranes. (1) Carboranes from the reaction of decarborane with acetylenic compounds," norg. Chem. 2:1089–1092 (1963).

Hogrefe, et al., "Deprotection of methylphosphonate oligonucleotides using a novel one–pot procedure," Nucleic Acids, Research, 21:9, pp. 2031–2038.

Holy, A., "2'–Deoxy–L–Uridine," *Nucleic Acid Chemistry*, (1986) Townsend LB, Tipson RS, ed. Part One, pp. 347–353.

Ishiwata et al., "Synthesis and radiation dosimetry of 4–borono–=2–[$^{13}$ F]–DL–phenylalanine:a target compound for PET and boron neutron capture therapy," *Chem. Absts.*, (1991) 114:224582b, pp 412.

Kabalka, et al., "Boron–11 Magnetic Resonance Imaging and Spectroscopy; Tools for Investigating Pharmacokinetics for Boron Neutron Capture Therapy," *Clinical Aspects of Neutron Therapy*, (1989) Plenum Press, pp. 243–249.

Kane, et al., "Automated Synthesis of Carborane–Derived Homogeneous Oligophosphates: Reagents for Use in the Immunoprotein–Mediated Boron Neutron Capture Therapy (BNCT) of Cancer," *J. Am. Chem. Soc.*, (1993) 115, pp. 8853–8854.

Kane, et al., "Solution–Phase Synthesis of Boron–Rich Phosphates," *J. Org. Chem.*, (1993) 58, pp. 3227–3228.

Kane, et al., "Solution–Phase Segment Synthesis of Boron-Rich Peptides," *J. Org. Chem.*, (1993) 58, pp. 991–992.

Keane, et al., "Modulation of vinblastine (VB) cytotoxicity by dipyridamole (DPO verses tamoxifen (TAM): an in vivo preclinical study by subrenal capsule assay (SRCA) of human renal carcinoma (HRCC)," *Proceedings of the American Association for Cancer Research*, (1990) 31:2230, p. 376.

Lesnikowski, Z. J., "Stereocontrolled Sythesis of P–Chiral Analogues of Oligonucleotides," *Bioorganic Chem.*, (1993) 21, pp. 127–155.

Lesnikowski et al., "Carboranyl Oligonucleotides. 1. Synthesis of Thymidine (3',5') thymidine (o–Carboran–1–ylmethyl) phosphonate," *J. Org. Chem.*, (Nov. 1993) 58:24, pp. 6531–6534.

Lesnikowski, Z. J. et al., "Boron Neutron Capture Therapy of Cancers: Nucleic Bses, Bucleosids, and Oligonucleotides as Potential Boron Carriers," *Pol. J. Chem.* (1995), 69, pp. 827–840.

Mansuri et al., "Preparation of the Geometric Isomers of DDC, DDA, D4C and D4T as Potential Anti–HIV Agents," *Bioorg. Med. Chem. Lett.*, (1991) 1, pp. 65–68.

Marshall and Caruthers, "Phosphorodithioate DNA as a Potential Therapeutic Drug," *Science*, (1993) 259, pp. 1564–1570.

Milligan, et al., "Current Concepts in Antisense Drug Design," *J. Med Chem.*, (1993) 36:14, pp. 1923–1937.

Scjomazo. R. F., "N.Y. cancer patient fights for novel radiation therapy," *The Atlanta Journal/The Atlanta Constitution*, (Sep. 17, 1994), p. E8.

Nemoto, et al., "Design an synthesis of Boron–10 carriers for neutron capture therapy of cancer," *Chemical Abstracts*, (1994) 120:157638h, p. 513.

Peterson et al., "Synthesis and Biological Evaluation of 4–Purinylpyrrolidine Nucleosides," *J. Med. Chem.*(1991) 34, pp. :2787–2797.

Pettersson et al. "Accumulation of $^{10}$B in the Central Degenerative Areas of Human Glioma and Colon Carcinoma Spheroids after Sulfhydryl Boron Hydride Administration," *Cancer Research*, (Mar. 15, 1995) 52, pp. 1587–1591.

Prystas, M., et al. "Nucleic Acid Components and Their Analogues. XLII. Synthesis of Anomeric 5–IODO–2'–Deoxyuridines," *Collect. Czech. Chem. Commun.* (1964) 29, pp. 121–129.

Reynolds, et al., "2,4–Dichloro–5–(1–o–carboranylmethyl)–6–menthylpyrimidine: A Potential Synthon for 5–(1–o–Carboranylmethyl) pyrimidines," *J. Org. Chem.* (1991) 56:7, pp. 2391–2395.

Robins, et al. "Purine Nucleosides. XXIX. Synthesis of 2'–Deoxy–L–adenosine and 2'–Deoxy–L–guanosine and their α Anomers," *J. Org. Chem.*, (1992) 35:3, pp. 636–639.

Schinazi, et al. "Activities of 3'–Azido–3'–Deoxythymidine Nucleotide Dimers in Primary Lymphocytes Infected with Human Immunodeficiency Virus Type 1," *Antimicrobial Agents Chemother.*, (1990) 34:6: pp. 1061–1067.

Schinazi, et al. "Synthesis, Antiviral Activity, Cytotoxicity, and Cellular Pharmacology of 5–Carboranyl Pyrimidine Nucleosides," *Advances in Neutron Capture Therapy*, Soloway, A.H.; Barth, F. R.; Carpenter, D.E., Eds.; Plenum Press; New York and London (1003), pp 285–288.

Schinazi, et al. "Synthesis of 5-(Dihydroxyboryl)-2'-deoxyuridine and Related Boron-Containing Pyrimidines," *J. Org. Chem.* (1985) 50, pp. 841–847.

Schinazi, et al. "Synthesis, Biological Activity and Cellular Pharmacology of 5-Carboranyl-Pyrimidine Nucleosides," *Tenth International roundtable: Nucleosides and Nucleotides, Park City, Utah*; (1992), p. 28.

Schinazi, et al., "Carboranyl Oligonucleotides for Antisense Technology and Boron Neutron Capture Therapy of Cancers," *Carbohydrate Modifications in Antisense Res.*, (1994) Chpt. 11, pp. 169–182.

Schinazi, et al., "Synthesis and Properties of Boron and Silicon Substituted Uracil or 2-Deoxyuridine," *Tetrahedron Letters*, (1978) 50, pp. 4981–4984.

Schwemmer. et al., "Specific Androcen Uptake In Rat Prostate and R3327 Rat Prostate Carcinoma: A Prerequisite for the Use of Borated Androgens in Boron Neutron Capture Therapy," *Tetrahedron Letters*, (1987) *J. of Urology*, 137:4/2, 1020.

Shibarahara S., et al. "Inhibition of human immunodeficiency virus (HIV01) replication by synthetic oligo-RNA derivatives," *Nucleic Acids Research*, (1989) 17:1, pp. 239–253.

Sood, et al. "Boron–Containing Nucleic Acids: Synthesis of Cyanoborane Adducts of 2'–Deoxynucleosides," *J. Am. Chem. Soc.* (1989) 111, pp. 9234–9235.

Sood, et al. "Boron–Containing Nucleic Acids. 2. Synthesis of Oligodeoxynucleoside Boranophosphates," *J. Am. Chem. Soc.* (1990) 112, pp. 9000–9001.

Su, et al. "Nucleosides. 136. Synthesis and Antiviral Effects of Several 1–(2–Deoxy–2–fluoro–β–D–arabinofuranosyl)–5–alkylu racils. Some structure–Activity Relationships," *J. Med. Chem.*, (1986) 29, pp. 151–154.

Tjarks, et al. "Synthesis and in Vitro Evaluation of Boronated Uridine and Glucose Derivatives for Boron Neutron Capture Therapy," *J. Med. Chem.* (1992) 35, pp. 1628–1633.

Tolphin, et al. "Boron Neutron Capture Therapy of Cerebral Gliomas," *Oncology*, (1975) 32, pp. 223–246.

Uhlmann and Peyman, "Antisense Oligonucleotides: A New Therapeutic Principle," *Chemical Reviews*, (Jun. 1990) 90:4, pp. 544–584.

Van Roey, et al., "Absolute configuration of the antiviral agent (-)-cis-5-fluoro-1-[2-hydroxymethyl)-1,3-oxithionlan-5-yl]cytosine," *Antiviral Chemistry & Chemotherapy* (1993) 4:6, pp. 369–375.

Verrijk, R., et al. "Pharmacokinetics in melanoma-bearing mice of 5-dihydroxyboryl-6-propyl-2-thiouracil (BPTU), a candidtate compound for boron neutron capture therapy," *Br. J. Cancer* (1994), 69:4, pp. 641–647.

Vorbruggen, H., et al., "On the Mechanism of Nucleoside Synthesis," *Chemische Berichte* (1981) 114, pp. 1256–1268.

Whale, et al. "The Synthesis and Antiviral Activity of (E)-5-(2-Nitrovinyl) Uridine and (E)-5-(2-Nitrovinyl)-2'-Deoxyuridine," *Nucleosides & Nucleotides*, 111(2–4):595–602 (1992).

Wilson, J. Gerald, "Synthetic Approaches to a Carboranyl Thiouracil," *Pigment Cell Res.*, (1998) 2, pp. 297–303.

Wilson and Liotta, "A General Method for Controlling Glycosylation Stereochemistry in the Synthesis of 2'-Deoxyribose Nucleosides," *Tetrahedron Letters* (1990) 31:13, pp. 1815–1818.

Yamamoto, et al., "Synthesis of Carboranes Containing Nucleoside Bases. Unexpectedly High Cytostatic and Cytocidal Toxicity towards Cancer Cells," *J. Chem. Soc., Chem. Com.*, 157–158 (1992).

Yamamoto, et al., "Boron–10 Carriers for NCT. A New Synthetic Method Via Condensation with Aldehydes Having Boronic Moiety," *Tetrahedron Lett.*, 30:7191–7194 (1989).

Yamamoto, et al., "Synthesis of Carbonanes Containing Nucleoside Bases," *Heteroatom Chem.*, 3(3):239–244 (1992).

Zamenhof, et al., "BNCT: Looking for a few good Molecules," *J. Nat'l. Cancer Inst.*, 84:1290–1291 (1992).

Zoltewicz and Jacobson, "Nucleophilicities of Compounds with Interacting electron Pairs. Diazine–Catalyzed Ester Hydrolysis," Tetrehedron Letters, 2:189–192(1972).

I. DMT Cl/pyridine; II. [(CH₃)₂CH]₂NP(Cl)OCH₂CH₂CN/diisopropylethylamine, methylene chloride x = 9 or 10

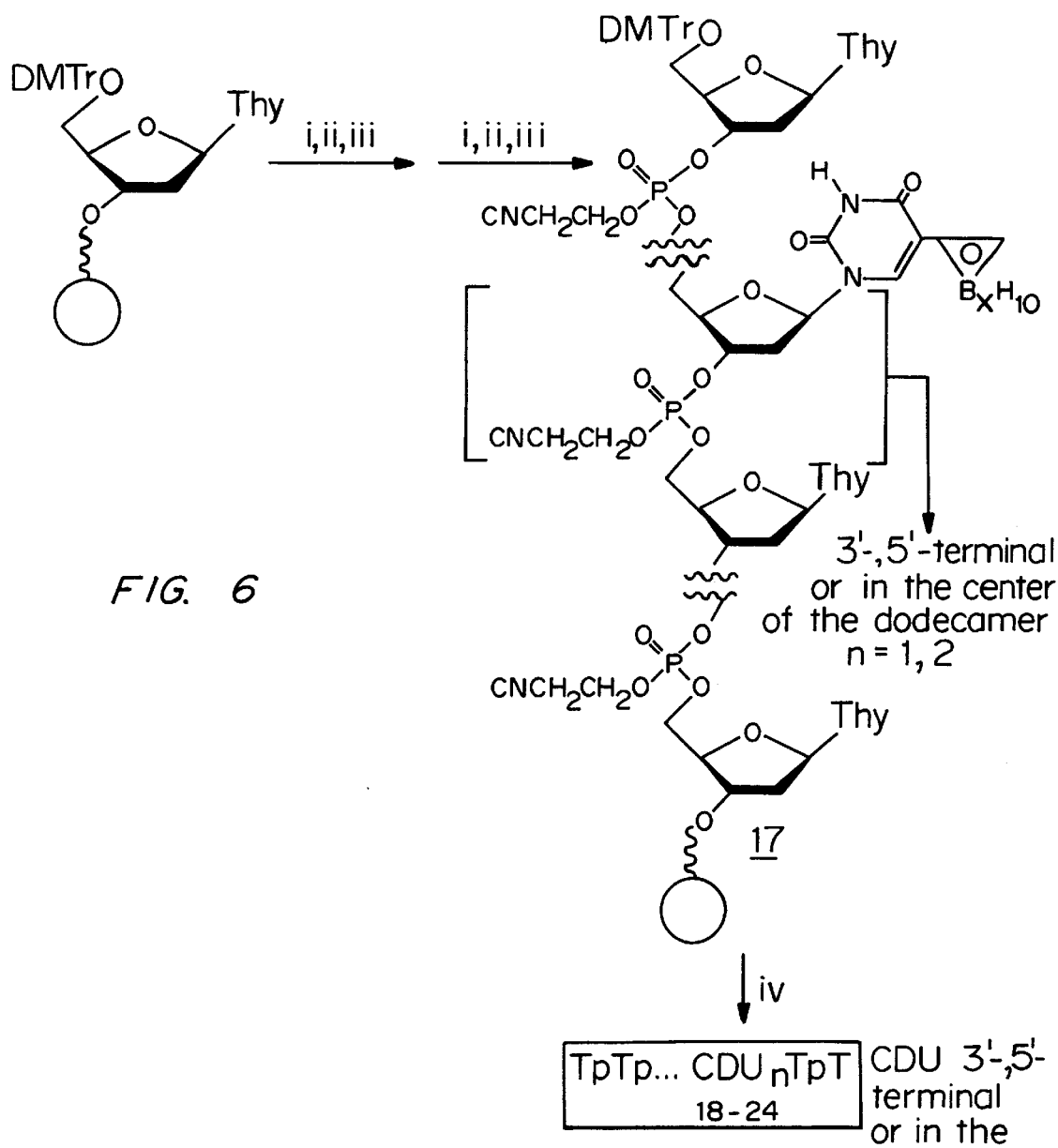
FIG. 6
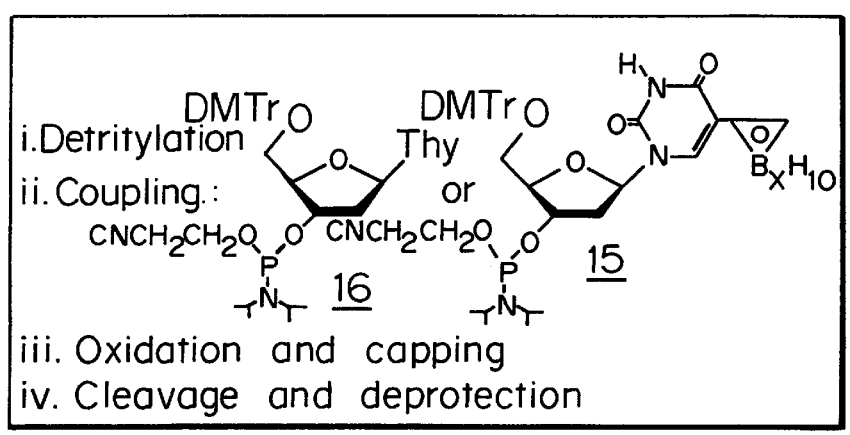
i. Detritylation
ii. Coupling
iii. Oxidation and capping
iv. Cleavage and deprotection

```
                         SEQUENCE LISTING (1) GENERAL INFORMATION:

(iii) NUMBER OF SEQUENCES: 18

(2) INFORMATION FOR SEQ ID NO: 1:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (synthetic)

(iii) HYPOTHETICAL: NO (iv) ANTI-SENSE: YES (ix) FEATURE:
         (A) NAME/KEY: misc_feature
         (B) LOCATION: 11
         (D) OTHER INFORMATION: /function= "N = CDU"

(x) PUBLICATION INFORMATION:
         (A) AUTHORS: Schinazi, Richard F.
                     Lesnikowski, Zbigniew J.
         (K) RELEVANT RESIDUES IN SEQ ID NO:1: FROM 1 TO 20

(xi) SEQUENCE DESCRIPTION: SEQ ID NO: 1:

AATACATGGA NGATTTGTAT                                                 20

(2) INFORMATION FOR SEQ ID NO: 2:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (synthetic)

(iii) HYPOTHETICAL: NO (iv) ANTI-SENSE: YES (ix) FEATURE:
         (A) NAME/KEY: misc_feature
```

(B) LOCATION: 10..11
            (D) OTHER INFORMATION: /function= "N is CDU"

(xi) SEQUENCE DESCRIPTION: SEQ ID NO: 2:

AATACATGGN NGATTTGTAT                                               20

(2) INFORMATION FOR SEQ ID NO: 3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 3:

ATACAAATCA TCCATGTATT                                               20

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 4:

ATACAAATCA ACCATGTATT                                               20

(2) INFORMATION FOR SEQ ID NO: 5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (iv) ANTI-SENSE: NO (ix) FEATURE:
        (A) NAME/KEY: misc_feature
        (B) LOCATION: 1..19
        (D) OTHER INFORMATION: /function= "N is CDU."

(xi) SEQUENCE DESCRIPTION: SEQ ID NO: 5:

NACACCCAAT TCTGAAATNG                                               20

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (x) PUBLICATION INFORMATION:
             (A) AUTHORS: Shibahara S. et al.
             (C) JOURNAL: Nucleic Acid Research
             (D) VOLUME: 17
             (F) PAGES: 239-240
             (G) DATE: 1989
             (K) RELEVANT RESIDUES IN SEQ ID NO:10: FROM 1 TO 20

(xi) SEQUENCE DESCRIPTION: SEQ ID NO: 6:

GACACCCAAT TCTGAAATGG                                                         20

(2) INFORMATION FOR SEQ ID NO: 7:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 7:

GCACCCATCG ACGTCCAACC                                                         20

(2) INFORMATION FOR SEQ ID NO: 8:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 8:

CAATTTCAGA ATTGGGTGTA                                                         20

(2) INFORMATION FOR SEQ ID NO: 9:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 9:

CCATTTCAGA ATTGGGTGTC                                                         20

(2) INFORMATION FOR SEQ ID NO: 10:

(i) SEQUENCE CHARACTERISTICS:
             (A) LENGTH: 20 base pairs

```
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (iv) ANTI-SENSE: NO (ix) FEATURE:
        (A) NAME/KEY: misc_feature
        (B) LOCATION: 1..19
        (D) OTHER INFORMATION: /function= "N is CDU."

(x) PUBLICATION INFORMATION:
        (A) AUTHORS: Marshall, W. S.
              Caruthers, M. H.
        (C) JOURNAL: Science
        (D) VOLUME: 259
        (F) PAGES: 1564-1565
        (G) DATE: 1993
        (K) RELEVANT RESIDUES IN SEQ ID NO:10: FROM 1 TO 20

(xi) SEQUENCE DESCRIPTION: SEQ ID NO: 10:

NCCCTGTTCG GGCGCCACNG                                                  20

(2) INFORMATION FOR SEQ ID NO: 11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 11:

TCCCTGTTCG GGCGCCACTG                                                  20

(2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 12:

CAGTGGCGCC CGAACAGGGA                                                  20

(2) INFORMATION FOR SEQ ID NO: 13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO
```

(iv) ANTI-SENSE: NO (xi) SEQUENCE DESCRIPTION: SEQ ID NO: 13:

GGCGCTTGTG GAGAAGGAGT TC                                                    22

(2) INFORMATION FOR SEQ ID NO: 14:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (synthetic)

(iii) HYPOTHETICAL: NO (iv) ANTI-SENSE: NO (ix) FEATURE:
            (A) NAME/KEY: misc_feature
            (B) LOCATION: 1..19
            (D) OTHER INFORMATION: /function= "N is CDU."

(xi) SEQUENCE DESCRIPTION: SEQ ID NO: 14:

NGCGCTTGTG GAGAAGGAGT NC                                                    22

(2) INFORMATION FOR SEQ ID NO: 15:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 15:

TGAGATGCCG TCGAGGATGT ACC                                                   23

(2) INFORMATION FOR SEQ ID NO: 16:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (synthetic)

(iii) HYPOTHETICAL: NO (iv) ANTI-SENSE: NO (ix) FEATURE:
            (A) NAME/KEY: misc_feature
            (B) LOCATION: 1..19

(ix) FEATURE:
            (A) NAME/KEY: misc_feature
            (B) LOCATION: 1..19
            (D) OTHER INFORMATION: /function= "N is CDU."

(xi) SEQUENCE DESCRIPTION: SEQ ID NO: 16:

NGAGATGCCG TCGAGGATGT ANC                                                   23

(2) INFORMATION FOR SEQ ID NO: 17:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 17:

TGGACTGCAG GAACTCCTT                                                    19

(2) INFORMATION FOR SEQ ID NO: 18:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (iv) ANTI-SENSE: NO (ix) FEATURE:
        (A) NAME/KEY: misc_feature
        (B) LOCATION: 1..18
        (D) OTHER INFORMATION: /function= "N is CDU."

(xi) SEQUENCE DESCRIPTION: SEQ ID NO: 18:

NGGACTGCAG GAACTCCNT                                                    19

NUCLEOSIDES AND OLIGONUCLEOTIDES CONTAINING BORON CLUSTERS

This is a divisional application of U.S. patent application Ser. No. 08/161,674 filed on Dec. 2, 1993 by Raymond F. Schinazi, Geraldinine Fulcrand-el Kattan and Zbigniew Jan Lesnikowski, now U.S. Pat. No. 6,180,766.

This invention is in the area of synthetic organic chemistry, and is in particular carboranyl containing synthetic nucleosides and oligonucleotides, and their method of preparation and use.

BACKGROUND OF THE INVENTION

The goal of cancer therapy is to achieve a degree of selectivity that spares normal cells and destroys all malignant ones, since even a small number of remaining malignant cells can lead to recurrence, metastasis, and death. A two-component or binary system comprised of constituents that alone are nonlethal and largely confined to malignant cells, and which when combined are lethal to the neoplastic cells yet innocuous to normal cells is an ideal modality. One advantage of this type of binary system is that each component can be manipulated independently to maximize selectivity.

Boron neutron capture therapy (BNCT, see FIG. 1) is a binary system which combines two separately nonlethal constituents, a radiosensitizing compound that contains a stable boron-10($^{10}$B) isotope, and nonionizing neutron radiation. When boron-10 is irradiated with neutrons, a nuclear reaction occurs that yields helium nuclei (α-particle), lithium nuclei, and about 100 million times more energy than the initial irradiated energy. The generated radiation destroys malignant cells containing the boron compound. Selectivity is achieved through the use of compounds which accumulate primarily in malignant cells and/or by aiming the neutron beam at the tumor mass which contains the boron carrier.

The major obstacles in BNCT are: (1) the achievement of a sufficiently high intracellular boron concentration and (2) selectivity toward tumor cells. Although attempts to develop tumor-selective boron compounds date back to the 1960s and despite extensive studies, the problem of selective delivery of boron carriers to tumor cells remains.

Many classes of compounds have been synthesized for BNCT. For example, see Barth, R. F.; Soloway, A. H.; Fairchild, R. G.; Brugger, R. M. *Cancer* 1992, 70, 2995–3008; Fairchild, R. G.; Kahl, S. B.; Laster, B. H.; Kalef-Ezra, J.; Popenoe, E. A. *Cancer Res.* 1990, 50, 4860–4865; and Zamenhof, R. G.; Kalend, A. M.; and Bloomer, W. D. *J Natl Cancer Inst* 1992, 84, 1290–1291.

The first boron-containing nucleoside, 5-dihydroxyboryl-2'-deoxyuridine, was synthesized by Schinazi and Prusoff in 1978. Schinazi, R. F., Prusoff, W. H. *Tetrahedron Lett* 1978, 4981–4984; and Schinazi, R. F.; Prusoff, W. H. *J Orgr Chem* 1985, 50, 841–847. Sood et al. have reported the synthesis of a series of cyanoborane adducts of 2'-deoxynucleosides, specifically 2'-deoxyguanosine-N$^7$-cyanoborane, 2'-deoxyinosine-N$^7$-cyanoborane, 2'-deoxyadenosine-N$^1$-cyanoborane, and-2'-deoxycytidine-N$^3$-cyanoborane. Sood, A.; Spielvogel, B. F.; Shaw, B. R. *J Am Chem Soc* 1989, 111, 9234–9235.

Sood et al. have also reported the synthesis of oligonucleotides with a boronated internucleotide backbone, in the form of boranophosphates and boranophosphate methyl esters. The borane (BH$_3$) group in these boronated oligonucleotides is isoelectronic and isostructural with normal O-oligonucleotides and oligonucleotide methylphosphonates. Sood, A.; Shaw, B. R.; Spielvogel, B. F. *J Am Chem Soc* 1990, 112, 9000–9001. The Sood compounds in general have a low boron content and some have lower than desired lipophilicity.

U.S. Pat. No. 5,130,302 to Spielvogel, et al., discloses a novel class of boronated nucleosides, nucleotides and oligonucleotides for use as antineoplastic, antiinflammatory, and antihypertensive agents. The nucleosides, nucleotides and oligonucleotides are covalently attached to either BH$_2$CN, BH$_3$, or BH$_2$CO$_2$R moieties, wherein R is C$_1$ to C$_{18}$ alkyl.

A number of carboranyl pyrimidines have been prepared for use in boron neutron capture therapy. Examples of carboranyl pyrimidines include 5-(3-o-carboranylpropyl-6-methyl-2-thiouracil (compound A) (Wilson, J. G. *Pigment Cell Res* 1989, 2, 297–303), 2,4-dichloro-5-(1-o-carboranylmethyl)-6-methylpyrimidine; (compound B) (Reynolds, R. C.; Trask, T. W.; Sedwick, W. D. *J Org Chem* 1991, 56, 2391–2395); and 5-carboranyluracil (compound C) (Goudgaon, N. M.; El-Kattan, Y.; Fulcrand, G.; Liotta, D. C.; Schinazi, R. F. IMEBORON VIII, Knoxyille, Tenn.; p72, 1993).

Purine and pyrimidine nucleosides that contain a carboranyl group attached to the purine or pyrimidine base have also been reported. Yamamoto, Y.; Seko, T.; Nakamura, H. *Heteroatom Chem* 1992, 3, 239–244; and Schinazi, R. F.; Goudgaon, N. M.; Soria, J.; Liotta, D. C. 5th International Symposium on Neutron Capture Therapy, Columbus, Ohio; p11, 1992; Schinazi, R. F.; Goudgaon, N.; Soria, J.; Liotta, D. C. Tenth International Roundtable: Nucleosides and Nucleotides, Park City, Utah; p28, 1992. These compounds are lipophilic and some are readily phosphorylated by cellular kinases, and in certain cells can incorporate into DNA as analogues of natural 2'-deoxypyrimidine nucleosides. Examples include 5-carboranyl-2'-deoxyuridine (compound D, CDU), 5-carboranyluridine (compound E, CU), 5-(1-hydroxymethyl)carboranyluridine, and 5-(1-hydroxymethyl)carboranyluridine (compound F, HMCU).

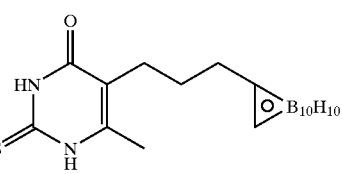

A

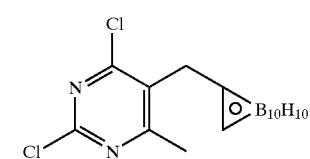

B

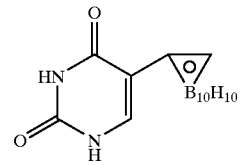

C

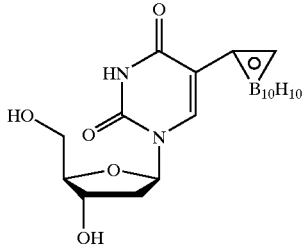

D

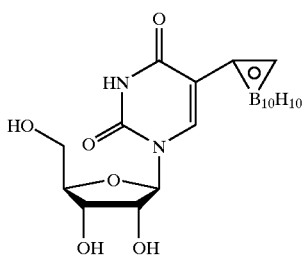

E

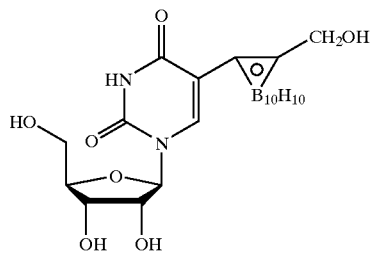

F

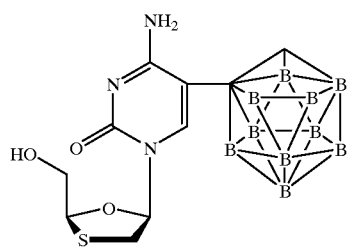

G

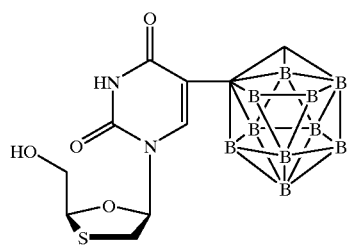

H

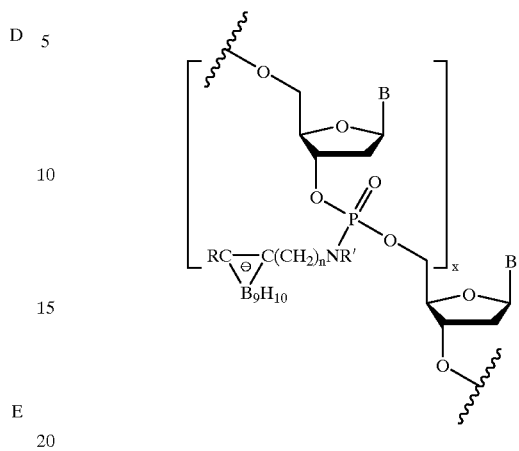

I

PCT WO 93/17028 filed by Raymond F. Schinazi and Dennis C. Liotta discloses a number of synthetic nucleosides that contain a carboranyl moiety covalently attached to a purine or pyrimidine base, wherein the sugar moiety optionally contains a second heteroatom in the 3'-position of the ring. Preferred compounds are 2-hydroxymethyl-5-(5-carboranylcytosin-1-yl)-1,3-oxathiolane (compound G) and 2-hydroxymethyl-5-(5-carboranyluridin-1-yl)-1,3-oxathiolane (compound H).

Powell, et al., recently reported the synthesis of oligonucleotides that contain 3',5'-nido-o-carboranyl-phosphoramidate linkages (compound I). While the oligonucleotide could reportedly localize in the cell nucleus, the boron moiety is acid labile because it is linked to the phosphorus atom through an amide-type bond.

The requirements for efficient BNCT with oligonucleotides, which include cell selectivity (ability to accumulate preferentially in diseased cells), stability of the chemotherapeutic agent in vivo (resistance against digestion by cellular nucleases and chemical stability), and transportability. (ability of the chemotherapeutic agent to pass easily through cellular membranes), are very similar to the requirements for Antisense oligonucleotide Technology (AOT), another recently developed therapy for cancer as well as other diseases. Uhlmann, "Antisense Oligonucleotides: A New Therapeutic Approach" *Chemical Reviews,* 90(4), June 1990. The compounds should also be relatively non-toxic. Antisense technology refers in general to the modulation of gene expression through a process wherein a synthetic oligonucleotide is hybridized to a complementary nucleic acid sequence to inhibit transcription or replication (if the target sequence is DNA), inhibit translation (if the target sequence is RNA) or to inhibit processing (if the target sequence is pre-RNA). A wide variety of cellular activities can be modulated using this technique. A simple example is the inhibition of protein biosynthesis by an antisense oligonucleotide bound to mRNA. In another embodiment, a synthetic oligonucleotide is hybridized to a specific gene sequence in double stranded DNA, forming a triple stranded complex (triplex) that inhibits the expression of that gene sequence. Antisense oligonucleotides can be also used to activate gene expression indirectly by suppressing the biosynthesis of a natural repressor or directly by reducing termination of transcription. AOT can be used to inhibit the expression of pathogenic genes, for example, those that facilitate the replication of viruses, including human immunodeficiency virus (HIV), hepatitis B virus (HBV), and herpesviruses, and cancers, particularly solid tumor masses such as gliomas, breast cancer, and melanomas.

While progress has been made in the areas of both BNCT and AOT, none of the synthetic oligonucleotides prepared to date exhibit the optimal combination of cell selectivity, stability in vivo, and ability to pass easily through cellular membranes (transportability).

Therefore, it is an object of the present invention to provide a new class of synthetic oligonucleotides for use in BCNT, AOT, or both, that exhibit a desired profile of cell selectivity, stability in vivo, and ability to pass easily through cellular membranes.

It is another object of the present invention to provide new methods for the preparation of boron-containing nucleosides and oligonucleotides.

SUMMARY OF THE INVENTION

Carboranyl-containing nucleosides and oligonucleotides are provided for use in boron neutron capture therapy (BNCT) that are lipophilic and have a high content of boron atoms. In one embodiment, dinucleotides and oligonucleotides are provided that contain at least one uncharged 3',5'-O,O-[(carboran-1-yl-methyl)phosphonate] internucleotide linkage in place of the naturally occurring 3',5'-O,O-phosphodiester residue. The (carboran-1-yl-methyl) phosphonate linkage is not degraded by nucleases, and therefore, dinucleotides and oligonucleotides that contain the 3',5'-O,O-[(carboran-1-yl-methyl)phosphonate] internucleotide linkage are stable in biological fluids and cells. In light of the fact that oligonucleotides are primarily degraded by 3'-exonucleases, in a preferred embodiment, oligonucleotides are provided in which the two terminal nucleosides at the 3'-end, or nucleosides adjacent to these nucleosides, are linked via the nuclease-stable 3',5'-O,O-[(o-carboran-1-yl-methyl)phosphonate] bridge. The 3',5'-O,O-[(o-carboran-1-yl-methyl)phosphonate] bridge is also stable in acidic environments and is highly thermally stable.

Oligonucleotides can be designed for BNCT according to methods described herein that are complementary to overexpressed or unique RNA or DNA sequences in target cancer cells, as a means to selectively accumulate the boron-containing material into these cells. Oligonucleotides of specific gene sequences that include one or more 3',5'-linking-(carboran-1-yl)phosphonate moieties can also be used in antisense therapy in the selective modification of gene expression.

In a second embodiment, nucleosides are provided that bear a (carboran-1-yl)phosphonate moiety in the 3' and/or 5'-position. These synthetic nucleotides are useful in boron neutron capture therapy, and selected compounds can exhibit activity against viruses such as HIV and HBV.

In another embodiment, oligonucleotides are provided that bear a carboranyl-modified base in at least one of the nucleosides of the oligomer. In a preferred embodiment, the carboranyl-containing base is in a nucleoside located at the 3'-terminus, in the nucleoside adjacent to the 3'-terminal nucleoside, in the 5'-terminal nucleoside, or in the nucleoside adjacent to the 5'-terminal nucleoside. oligonucleotides bearing carboranyl-containing bases in the 3'-terminal nucleoside or the nucleoside adjacent to the 3'-terminal are more resistant to degradation by 3'-exonucleases. It has been discovered that olignucleotides bearing carboranyl-containing base units in the preferred positions hybridize more effectively to complementary nucleic acid sequences than oligonucleotides bearing carboranyl-containing bases in other positions.

In yet another embodiment, oligonucleotides are provided that bear at least one 3',5'-[(O,O-carboran-1-yl)phosphonate] residue and at least one nucleoside that contains a carboranyl-containing base, as a means to increase the boron density and lipophilicity of the molecule, and depending on the location of the modifications, increase the stability of the oligomer in vivo in biological fluids or cells.

In another embodiment of the invention, nucleosides and oligonucleotides bearing an —O-[(carboran-1-yl)alkyl] phosphate, S-[(carboran-1-yl)alkyl]phosphorothioate, or Se-[(carboran-1-yl)alkyl]phosphoroselenoate in place of the (carboran-1-yl)phosphonate moiety are provided.

In addition to the use of the oligonucleotides described herein in BNCT, the oligomers disclosed herein can be used in vitro to carry out structure-activity relationships on the bulk tolerance of hybridization of synthetic oligonucleotides with complementary nucleic acid sequences, in MRI imaging, or as probes in a variety of diagnostic techniques.

Carboranyl-containing oligonucleotides can also be used to effect mutation of expressed HIV-1 reverse transcriptase, using in vitro or in vivo Site Directed Mutagenesis (SDM).

Nucleosides, nucleotides, and oligonucleotides can be prepared that contain boron clusters as a means to enhance lipophilicity wherein the boron is not enriched in $^{10}$B, but instead, in the $^{11}$B isotope. The nucleosides, nucleotides, and oligonucleotides of the present invention that are used for BNCT or other diagnostic techniques that depend on neutron radiation decay for the destruction of diseased cells or for signaling purposes should be enriched with a suitable amount of $^{10}$B, normally approximately 90–100% $^{10}$B, and typically between 92–96% $^{10}$B.

A novel process is provided for the preparation of nucleosides, dinucleotides, and oligonucleotides containing an (carboran-1-yl-methyl)phosphonate moiety via the key starting material O-methyl(carboran-1-yl)methyl phosphonate.

BRIEF DESCRIPTION OF THE FIGURES

FIG. 6 is an illustration of a process for the automated preparation of dodecathymidylic acid analogues bearing one or more 5-(o-carboran-1-yl)uracil residues, as further described in Table 1.

DETAILED DESCRIPTION OF THE INVENTION

Figure 1:
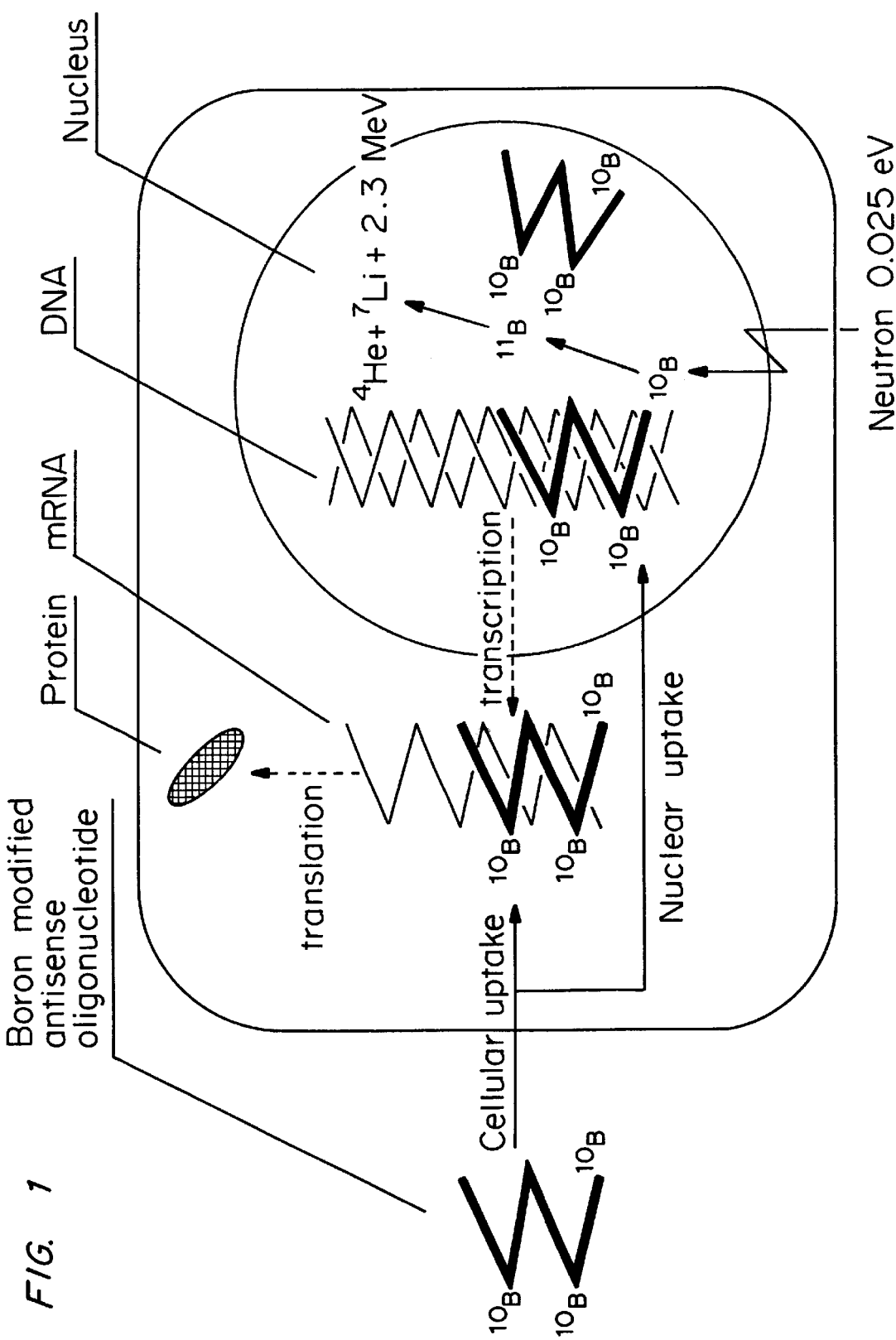
FIG. 1 is a schematic illustration of a hypothetical mechanism of action of boronated oligonucleotides for BNCT.

The term alkyl, as used herein, unless otherwise specified, refers to a saturated straight, branched, or cyclic, primary, secondary, or tertiary hydrocarbon of $C_1$ to $C_{10}$, and specifically includes methyl, ethyl, propyl, isopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The alkyl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991. The term lower alkyl, as used herein, and unless otherwise specified, refers to a $C_1$ to $C_4$ saturated straight or branched alkyl group.

The term alkylamino or arylamino refers to an amino group that has one or two alkyl or aryl substituents, respectively.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

The term aryl, as used herein, and unless otherwise specified, refers to phenyl, biphenyl, or naphthyl, and preferably phenyl. The aryl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991.

The term alkaryl or alkylaryl refers to an alkyl group with an aryl substituent.

The term aralkyl or arylalkyl refers to an aryl group with an alkyl substituent.

The term halo, as used herein, includes chloro, bromo, iodo, and fluoro.

The term purine or pyrimidine base includes, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^2$-alkyl-6-thiopurines, thymine, cytosine, 6-azapyrimidine, 2- and/or 4-thiopyrmidine, uracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, pyrazolopyrimidinyl. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, acyl groups such as acetyl and propionyl, methylsulfonyl, and p-toluylsulfonyl.

The term heteroaryl or heteroaromatic, as used herein, refers to an aromatic moiety that includes at least one sulfur, oxygen, or nitrogen in the aromatic ring. Nonlimiting examples are furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, pyridazinyl, pyrazinyl, cinnolinyl, phthalazinyl, quinoxalinyl, xanthinyl, hypoxanthinyl, and pteridinyl. Functional oxygen and nitrogen groups on the heterocyclic base can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methylsulfonyl, and p-toluylsulfonyl.

The term alkenyl, as referred to herein, and unless otherwise specified, refers to a straight, branched, hydrocarbon of $C_2$ to $C_{10}$ with at least one double bond.

The term acyl refers to moiety of the formula —C(O)R', wherein R' is alkyl; alkoxyalkyl including methoxymethyl; arylalkyl including benzyl; aryloxyalkyl such as phenoxymethyl; aryl including phenyl optionally substituted with halogen, $C_1$ to $C_4$ alkyl or $C_1$ to $C_4$ alkoxy, or the residue of an amino acid.

The term enantiomerically enriched, as used herein, refers to a compound that is a mixture of enantiomers in which one enantiomer is present in excess, and preferably present to the extent of 95% or more, and more preferably 98% or more, in the mixture.

The term oligonucleotide refers to an oligomer of thirty-five or less nucleotides linked through their 3' and 5'-hydroxyl or 2'- and 5'-hydroxyl groups.

The term amino acid includes naturally occurring and synthetic amino acids, and includes but is not limited to, alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaoyl, lysinyl, argininyl, and histidinyl.

It should be understood that when the term (carboran-1-yl)phosphonate is used in this text, it should be understood that —O-(carboran-1-yl)alkyl]phosphate, S-(carboran-1-yl)alkyl]phosphorothioate, or Se-(carboran-1-yl)alkyl] phosphoro-selenoate can be used in place thereof.

A new class of modified lipophilic nucleotides and oligonucleotides bearing carboranyl residues is provided for use in BNCT, AOT and for diagnostic purposes, including an MRI and as probes. The oligonucleotides bear one or more carboran-1-yl residues, allowing for the concentrated and selective. administration of boron to target cells. The lipophilicity of boron-modified oligonucleotides can be manipulated by the appropriate selection of the number and location of the carboran-1-yl residues in the compound. In general, a carboranyl group linked directly to a phosphorus atom or through an appropriate spacer (e.g., alkyl, peptidyl) attached to oxygen, sulfur, or selenium, has a more significant effect on the lipophilicity of the compound than when the carboranyl group is attached in another location, such as on the base, because it acts as a substitute for a hydrophilic and ionizable hydroxy group.

In one embodiment, the carboranyl-containing oligonucleotides are targeted specifically to cancer cells to inhibit the overexpression of certain protooncogenes or to optimize expression of tumor suppressor genes which correlate well with clinical progression of tumors, including gliomas, melanomas, and breast tumors.

Carboranyl Nucleosides and Nucleotides

A. The Carboranyl Moiety

Carboranes (also referred to as carbaboranes) are compounds that contain carbon atoms incorporated into a polyhedral borane. For a review of carborane chemistry, see F. Cotton and G. Wilkinson, *Advanced Inorganic Chemistry*, Fourth Edition, John Wiley and Sons, 1980, pages 318–320. The CH group is isoelectronic with $BH^-$, and thus can replace a BH group. Polyhedral carboranes can thus be considered as formally derived from $B_nH_{n-2}$ ions, with two carbon replacements, leading to molecules of the general formula $B_{n-2}C_2H_{n+2}$. Neutral two carbon carboranes are generally of the formula $B_nC_2H_{n+2}$, wherein n is 3–10. For the purposes described herein, while any of these carboranes in any isomeric form can be used, carboranes wherein n=9 or 10 are preferred.

When the two carbon atoms are next to each other in the carborane framework, the carborane is referred to as a 1,2- or ortho-carborane (o-carborane). For example, $B_{10}C_2H_{12}$ is usually prepared as a 1,2-isomer, which when heated rearranges to a 1,7-isomer.

Carboranes can exist in a number of isomeric forms. "Closo" carboranes are closed cage structures, whereas "nido" carboranes are open nest-like structures. Examples are anionic o-nido-7,8-$C_2B_9H_{(11\ or\ 12)}$ and neutral o-closo-1,2-$C_2B_{10}H_{12}$. Carbaboranes can also exist as one of four arachno isomers or as a hypho-isomer. Both the 1,2- and the 1,7-dicarbadodecaboranes and their C-substituted derivatives, on treatment with strong base, are degraded with loss of boron to give isomeric nido-carborane anions, $B_9C_2H_{(11\ or\ 12)}$. Both isomeric $B_9C_2H_{(11\ or\ 12)}^-$ ions on treatment with anhydrous acid followed by heating are converted into the closo-carborane $B_9C_2H_{11}$. Carbaboranes are typically prepared by the interaction of boranes or borane adducts with acetylenes. The most common carboranes are $B_{10}C_2H_{12}$ and its carbon-substituted derivatives. Carbon-substituted carboranes can be prepared with substituted acetylenes, as known to those skilled in the art, or, for example, by reaction of the carbaborane with a strong base to replace a hydrogen with lithium, followed by treatment with a desired electrophilic reagent. Acetylene derivatives that can be used to provide substituted carborane moieties are described, for example, in Heying, T. L., et al. Inorganic Chemistry 2(6) 1089–1092, 1963).

Anionic carboranes can be administered as a pharmaceutically acceptable salt of a single or multivalent pharmaceutically acceptable cation, including but not limited to, zinc, calcium, bismuth, barium, magnesium, aluminum, copper, cobalt, nickel, cadmium, sodium, potassium, pyridinium, quaternary amine, ammonium, protonated ethylenediamine, or protonated amino acids, including but not limited to protonated lysine and protonated arginine.

B. Carboranyl Nucleosides and Nucleotides i). Nucleosides with (carboran-1-yl-methyl)phosphonate in the 3' or 5'-Position, or Both In one embodiment, a nucleoside is provided that contains an (carboran-1-yl-methyl)phosphonate in the 3' or 5'-position of the molecule. Nonlimiting examples are the nucleosides of Formulas I, II, and III illustrated below:

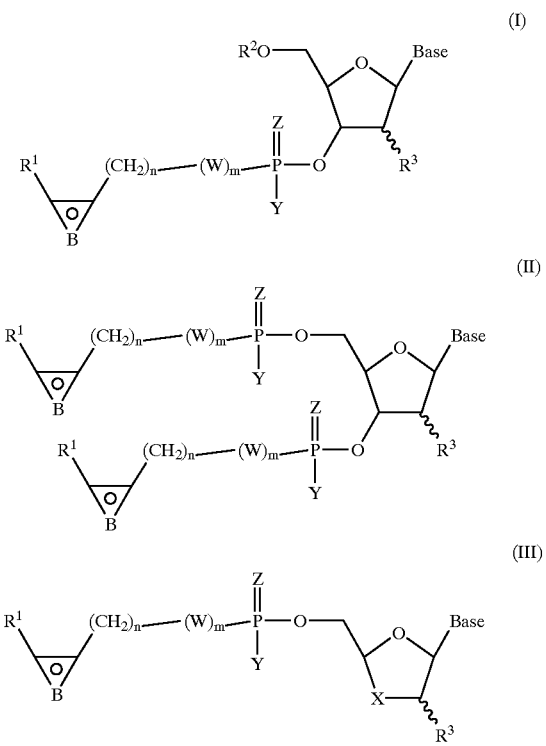

wherein:

$R^1$ is alkyl, haloalkyl, alkenyl, alkoxyalkyl, aryl, heteroaryl, trifluoromethyl, alkylaryl, arylalkyl, or halogen;

$R^2$ is hydrogen, alkyl, acyl (including acetyl); sulfonate ester including alkyl or arylalkyl sulfonyl including methanesulfonyl; a mono, di or triphosphate ester; trityl or monomethoxytrityl; benzyl, wherein the phenyl group is optionally substituted with one or more substituents as described in the definition of aryl given above; silyl, including trialkylsilyl (e.g. t-butyldimethylsilyl) or diphenylmethylsilyl; lipid; peptide; or cholesterol;

$R^3$ is hydroxyl, hydrogen, halogen, —CN, —$N_3$, lower alkyl, amino, alkylamino, dialkylamino, alkoxy; and wherein the $R^3$ group can be in the ribosyl ("down" with respect to the sugar moiety when orienting the ring such that the oxygen is in the back) or the arabinosyl ("up") conformation;

B represents the boron moiety of a carboranyl group, and specifically includes anionic o-nido-7,8-$C_2B_9H_{(11\ or\ 12)}$ and neutral o-closo-1,2-$C_2B_{10}H_{12}$;

W is O, S, or Se;

X is O, S, S(O), S(O)$_2$, CH$_2$, CHOH, CHN$_3$ or NH;

Y is OH, SH, SeH, or halogen, and in particular, fluorine;

n is 1–5; and m is 0 or 1.

The base is preferably a purine or pyrimidine base as defined above, and preferably is thymine, uracil, 5-halouracil including 5-fluorouracil, cytosine, 5-halocytosine including 5-fluorocytosine, adenine, guanine, 2,6-diaminopurine, 2-amino-6-chloropurine, 2-aminopurine, 5-lower alkyl uracil, or 5-lower alkylcytosine, 2-thiouracil, 2,4-thiouracil, 4-thiouracil, 6-chloropurine, 5-carboranyluracil, 5-carboranylcytosine and other carboranylpurines and carboranylpyrmidines, including those described in Section iv) below.

ii). Dinucleotides Containing an Uncharged 3',5'-OO-[(carboran-1-yl-methyl)phosphonate] Internucleotide Linkage In a second embodiment, a dinucleotide is provided wherein two nucleosides are connected via an uncharged 3',5'-O,O-[(carboran-1-yl-methyl)phosphonate] linkage. Nonlimiting examples are compounds of Formulas III and IV:

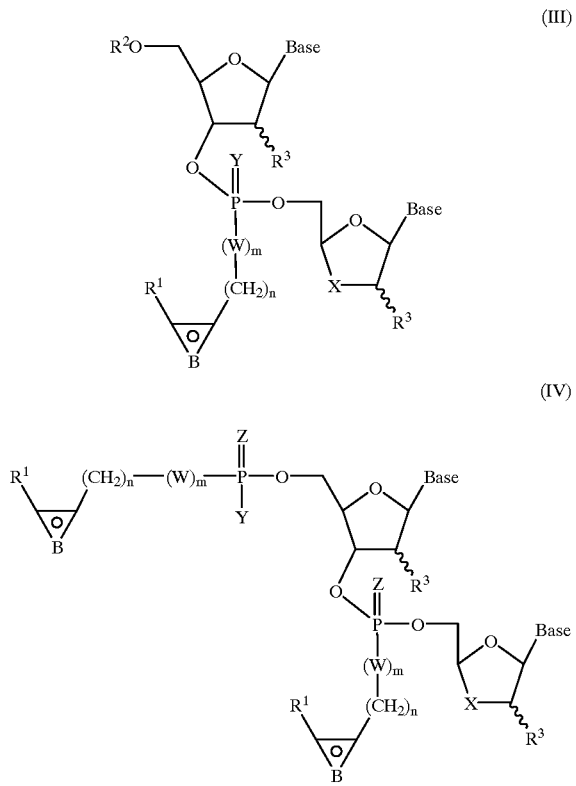

(III)

(IV)

wherein $R^1$, $R^2$, $R^3$, B, W, X, Y, Z, m and n are as defined above.

iii). Oligonucleotides Containing an Uncharged 31,5'-O,O-[(carboran-1-yl-methyl)phosphonate] Internucleotide Linkage In a third embodiment, oligonucleotides and phosphothioate or dithioate oligonucleotides, methylphosphonate oligonucleotides, and dephosphooligonucleotides (e.g., peptido-oligonucleotides) are provided that contain at least one 3',5'-O,O-[(carboran-1-yl-methyl)phosphonate] internucleotide linkage. The 3',5'-O,O -[(carboran-1-yl-methyl) phosphonate can link the terminal two nucleotides at the 3'-end of the oligonucleotide, the terminal two nucleotides at the 5'-end of the oligonucleotide, or, alternatively, two nucleotides in the internal section of the oligonucleotide, including adjacent ones. In light of the fact that most oligonucleotides are degraded by. 3'-exonucleases, in a preferred embodiment, an oligonucleotide is provided wherein a 3',5'-O,O-[(carboran-1-yl-methyl)phosphonate links at least the terminal two nucleotides at the 3'-terminus or the nucleosides adjacent to these.

The oligonucleotide, if desired, can contain more than one 3',5'-O,O -((carboran-1-yl-methyl)phosphonate linkage, up to a fully modified oligonucleotide. In a preferred embodiment, the oligonucleotide has between approximately one and five modified linkages for a typical (thirty or less)-mer.

Any of the purine or pyrimidine bases defined above can be used in the oligonucleotide, in any appropriate sequence, as discussed in more detail below. In one embodiment, naturally occurring nucleosides, such as adenosine, guanosine, cytidine, thymidine, or uridine, are present in the oligonucleotide.

A nucleotide can be used as the 3'-terminus that contains an X moiety, wherein X is O, S, S(O), S(O)$_2$, CH$_2$, or NH, and preferably O or S.

Synthetic oligonucleotides with 3',5'-O,O-[(carboran-1-yl-methyl)phosphonate] linkages of specific sequences can be prepared for hybridization to a complementary nucleic acid sequence to inhibit transcription or replication (if the target sequence is DNA) inhibit translation (if the target sequence is RNA), or to inhibit processing (if the target sequence is pre-RNA). Antisense carboranyl-modified oligonucleotides can be prepared, for example, that inhibit protein biosynthesis by hybridization to a target MRNA sequence, and for other purposes as described in the Background of the Invention.

Carboranyl-containing oligonucleotides can also be prepared that hybridize to a specific gene sequence in double stranded DNA to form a triple stranded complex (triplex) that inhibits the expression of that gene sequence.

A wide variety of nucleic acid sequences with known function have been reported, and given the extensive research currently being conducted in this area, many others will be reported in the future. Given the disclosure herein, one of ordinary skill in the art can prepare any nucleic acid sequence modified as desired with one or more 3',5'-O,O-[(carboran-1-yl-methyl)phosphonate] linkages for use in BCNT or AOT. It should be understood that this invention is not directed to specific nucleic acid sequences, but instead is a general technique to increase the stability, lipophilicity, transportability, and boron concentration of a sequence of interest.

iv). Oligonucleotides with Carboranyl Moiety in the Base

In a fourth embodiment, oligonucleotides are provided that contain a carboranyl moiety in a base unit of one of the nucleotides. Nonlimiting examples of carboranyl containing bases are illustrated in Formulas V through X.

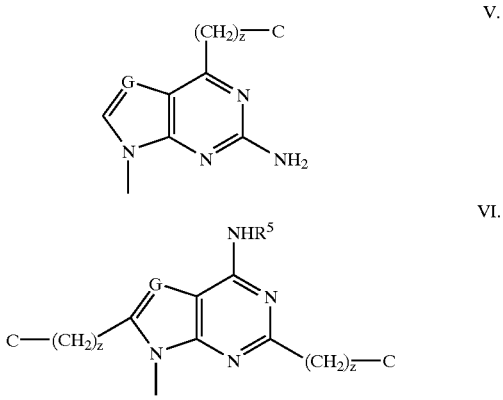

V.

VI.

-continued

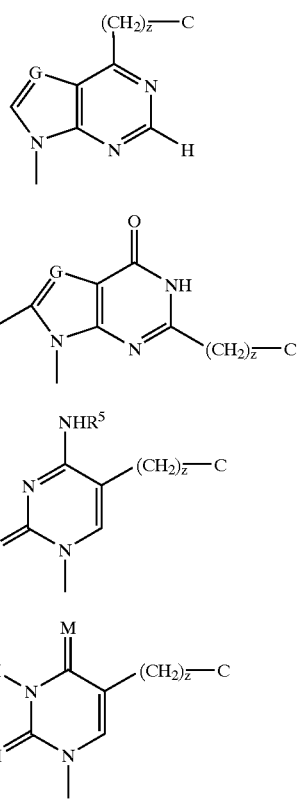

wherein:

VII. C is a carboranyl group such as $B_{10}H_{10}C_2R_4$, wherein $R_4$ is —H, —OH, —CH$_2$OH, —CH$_2$X (wherein X is halogen) or —B$_9$C$_2$H$_{(11\ or\ 12)}$ (a nido-carborane anion);
$R^5$ is lower alkyl;
G is N or CH;
M is O or S; and
z is 0 to 5.

The carboranyl-containing base can be in a 3'- or 5'-terminal nucleotide, in a nucleotide adjacent to the 3' or 5'-terminal nucleoside, or in an internal nucleotide. It has been discovered that oligonucleotides that contain carboranyl-modified bases in the 3'- or 5'-terminal nucleotide or in a nucleotide adjacent to the 3'- or 5'-terminal nucleoside hybridize more effectively to complementary nucleic acid sequences than oligonucleotides that bear carboranyl-containing bases in internal nucleotides. It has also been discovered that oligonucleotides that contain carboranyl-modified bases in the 3'-terminal nucleotide, in a nucleotide adjacent to the 3'-terminal nucleoside, or in both the 3'-terminal and 5'-terminal nucleosides are more resistant to degradation than those otherwise modified.

As discussed above in Section I. B. iii), it should be understood that any nucleic acid sequence of interest can be modified by addition of a carboranyl moiety to a base unit in the oligomer. This invention is not directed to specific nucleic acid sequences, but instead is a general technique.

EXAMPLE 1

DNA Sequences Containing 5-(o-carboran-1-yl)-2'—O-deoxyuridine

Examples of the modified DNA sequences (wherein X is 5-(o-carboran-1-yl)-2'—O-deoxyuridine, also referred to as CDU), as well as control sequences, are listed below. These examples are merely illustrative, and not intended to limit the scope of the invention.

DNA sequences

X = CDU [5-(o-carboran-1-yl)-2'-deoxyuridine]

For in viva site directed mutagenesis:
RL-1/CDU/Antigene          5'-AATACATGGAXGATTTGTAT-3'  (SEQ ID NO:1)

RL-2/CDU/Antigene          5'-AATACATGGXXGATTTGTAT-3'  (SEQ ID NO:2)

RL-1/Sense complimentary (SC)  5'ATACAAATCATCCATGTATT-3'  (SEQ ID NO:3)
                           (target sequence complementary to RL-1, it is also a
                           real, sense sequence)

RL- 2/SC                   5'-ATACAAATCAACCATGTATT-3'  (SEQ ID NO:4)
                           (target sequence complementary to RL-2)

Target for HIV-1
G/Z-1/CDU/AS               5'-XACACCCAATTCTGAAATXG-3'  (SEQ ID NO:5)  [HIV-splicing accep-
                           tor
                           site based on Shibahara S., et al. Nucleic Acids
                           Research, 17,239 (1989)]

G/Z-2/AS                   5'-GACACCCAATTCTGAAATGG-3'  (SEQ ID NO:6)
                           (as G/Z-1/CDU/AS but unmodified)

G/Z-3/R                    5'-GCACCCATCGACGTCCAACC-3'  (SEQ ID NO:7)  (random sequence,
                           Genejockey
                           version 1.0 Biosoft, 22 Hills Rd., Cambridge, CGZ ISP,
                           UK)

G/Z-1/S                    5'-CAATTTCAGAATTGGGTGTA-3'  (SEQ ID NO:8) (sequence complemen-
                           tary to
                           G/Z-1/CDU/AS)

G/Z-2/S                    5'-CCATTTCAGAATTGGGTGTC-3'  (SEQ ID NO:9) (BRU-LAV sequence, -continued DNA sequences complementary to G/Z-2/AS)

| | |
|---|---|
| G/Z-4/CDUAS | 5'-XCCCTGTTCGGGCGCCACXG-3' (SEQ ID NO:10) [HIV-RT primer binding site (PBS) Marshall WS & Caruthers, MH. Science 259, 1564, (1993)] |
| G/Z-5/UAS | 5'-TCCCTGTTCGGGCGCCACTG-3' (SEQ ID NO:11) (as G/Z-4/CDUAS but unmodified) |
| G/Z-6/S | 5'-CAGTGGCGCCCGAACAGGGA-3' (SEQ ID NO:12) |
| Target for Cancer Chemotherapy (gene suppression): | |
| IL6-A1 | 5'-GGCGCTTGTGGAGAAGGAGTTC-3' (SEQ ID NO:13) (22-mer) |
| IL6-A1/B | 5'-XGCGCTTGTGGAGAAGGAGTXC-3' (SEQ ID NO:14) (22-mer) |
| IL6-A2 | 5'-TGAGATGCCGTCGAGGATGTACC-3' (SEQ ID NO:15) (23-mer) |
| IL6-A2/B | 5'-XGAGATGCCGTCGAGGATGTAC-3' (SEQ ID NO:16) (23-mer) |
| IL6-A3 | 5'-TGGACTGCAGGAACTCCT-3' (SEQ ID NO:17) (19-mer) |
| IL6-A3/B | 5'-XGGACTGCAGGAACTCCXT-3' (SEQ ID NO:18) (19-mer) |

In an alternative embodiment, X is a nucleoside that contains a base illustrated in Section iv). In another alternative embodiment, the X represents an unmodified nucleotide such as thymidine, cytidine, adenosine, guanosine, or uridine, or its corresponding 2'-deoxynucleoside, and the above-identified sequences are modified instead by substitution of a 3',5'-O,O-[(carboran-1-yl-methyl)phosphonate linkage for a phosphodiester linkage (preferably at or close to the 3'-terminus), with or without base-carboranyl modification.

v). Oligonucleotides with Both a 3',5'-O,O-[(carboran-1-yl-methyl)phosphonate] Internucleotide Linkage and a Carboranyl-Containing Base In a fifth embodiment, oligonucleotides are provided that contain both a 3',5'-O,O-[(carboran-1-yl-methyl)phosphonate] internucleotide linkage and a carboranyl-containing base. The carboranyl-containing base can be on the same or different nucleotide than that linked via a 3',5'-O,O-[(carboran-1-yl-methyl)phosphonate] bridge.

B. Stereochemistry and Enantiomerism

The stereochemistry of the nucleotides and oligonucleotides presented herein is influenced by the configuration of the nucleosides and the configuration of the chiral (carboran-1-yl-methyl)phosphonate moiety, if present in the compound.

Stereochemistry of Nucleoside

In one embodiment, the oligonucleotides of the present invention are comprised of naturally occurring nucleosides, preferably adenosine, guanosine, cytidine, thymidine, and uridine that have been modified by addition of a 3',5'-O,O-((carboran-1-yl-methyl)phosphonate] linkage or by addition of a carboranyl moiety to one or more of the base units. The naturally occurring nucleosides have one stereochemical configuration that is set by nature. However, if a non-naturally occurring nucleoside is used in a oligonucleotide or alone, stereochemical issues become relevant. Since the 1' and 4' carbons of the sugar or modified sugar moiety (referred to below generically as the sugar moiety) of the synthetic nucleosides are chiral, their nonhydrogen substituents ($CH_2OR^2$ and the pyrimidine or purine base, respectively) can be either cis (on the same side) or trans (on opposite sides) with respect to the sugar ring system. The four optical isomers therefore are represented by the following configurations (when orienting the sugar moiety in a horizontal plane such that the "primary" oxygen (that between the C1' and C4'-atoms) is in back): cis (with both groups "up", which corresponds to the configuration of naturally occurring nucleosides), cis (with both groups "down", which is a non-naturally occurring configuration), trans (with the C1' substituent "up" and the C4' substituent "down"), and trans (with the C1' substituent "down" and the C4' substituent "up"). In general, "D-nucleosides" are cis nucleosides in a natural configuration and the "L-nucleosides" are cis nucleosides in the nonnaturally occurring configuration.

According to the present invention, synthetic nucleosides can be used in oligonucleotides or alone in any of these configurations. It is known that certain synthetic nucleosides can be more active, or less toxic, or both, in one configuration than in other configurations. One of ordinary skill in the art given this disclosure can easily determine the optimal stereochemical configuration for a specific synthetic nucleoside for a desired application. Alternatively, the nucleoside can be used as a racemic mixture or in the form of an enantiomerically enriched composition.

Enzymatic methods for the separation of D and L enantiomers of cis-nucleosides are disclosed in, for example, Nucleosides and Nucleotides, 12(2), 225–236 (1993); European Patent Application Nos. 92304551.2 and 92304552.0 filed by Biochem Pharma, Inc.; and PCT Publication Nos. WO 91/11186, WO 92/14729, and WO 92/14743 filed by Emory University.

Separation of the acylated or alkylated racemic mixture of D and L enantiomers of cis-nucleosides can also be accomplished by high performance liquid chromatography with chiral stationary phases, as disclosed in PCT Publication No. WO 92/14729.

α and β-L-Nucleosides can be prepared from methods disclosed in, or standard modifications of methods disclosed in, for example, the following publications: Jeong, et al., J. of Med. Chem., 36, 182–195, 1993; European Patent Application Publication No. 0 285 884; Genu-Dellac, C., G. Gosselin, A. -M. Aubertin, G. Obert, A. Kirn, and J. -L. Imbach, 3-Substituted thymine α-L-nucleoside derivatives as potential antiviral agents; synthesis and biological evaluation, *Antiviral Chem. Chemother.* 2:83–92 (1991); Johansson, K. N. G., B. G. Lindborg, and R. Noreen, European Patent Application 352 248; Mansuri, M. M., V. Farina, J. E. Starrett, D. A. Benigni, V. Brankovan, and J. C. Martin, Preparation of the geometric isomers of DDC, DDA, D4C and D4T as potential anti-HIV agents, *Bioorg. Med. Chem. Lett.* 1:65–68 (1991); Fujimori, S., N. Iwanami, Y. Hashimoto, and K. Shudo, A convenient and stereoselective synthesis of 2'-deoxy-β-L-ribonucleosides, *Nucleosides & Nucleotides* 11:341–349 (1992); Genu-Dellac, C., G. Gosselin, A. -M. Aubertin, G. Obert, A. Kirn, and J. -L. Imbach, 3-Substituted thymine α-L-nucleoside derivatives as potential antiviral agents; synthesis and biological evaluation, *Antiviral Chem. Chemother.* 2:83–92 (1991); Holy, A, Synthesis of 2'-deoxy-L-uridine, *Tetrahedron Lett.* 2:189–192 (1972); Holy, A., Nucleic acid components and their analogs. CLIII. Preparation of 2'-deoxy-L-ribonucleosides of the pyrimidine series. *Collect Czech Chem Commun.* 37:4072–4087 (1992); Holy, A, 2'-deoxy-L-uridine: Total synthesis of a uracil 2'-deoxynucleoside from a sugar 2-aminooxazoline through a 2.2'-anhydronucleoside intermediate. In: Townsend LB, Tipson RS, ed. Nucleic Acid Chem. New York: Wiley, 347–353. vol 1) (1992); Okabe, M., R. -C. Sun, S. Tan, L. Todaro, and D. L. Coffen, Synthesis of the dideoxynucleosides ddC and CNT from glutamic acid, ribonolactone, and pyrimidine bases. *J Org Chem.* 53:4780–4786 (1988); Robins, M. J., T. A. Khwja, and R. K. Robins. Purine nucleosides. XXIX. Synthesis of 2'-deoxy-L-adenosine and 2'-deoxy-L-guanosine and their alpha anomers. *J Org Chem.* 35:363–639 (1992); Genu-Dellac, C., Gosselin G., Aubertin A -M, Obert G., Kirn A., and Imbach J -L, 3'-Substituted thymine α-L-nucleoside derivatives as potential antiviral agents; synthesis and biological evaluation. *Antiviral Chem. Chemother.* 2(2):83–92 (1991); Genu-Dellac, C., Gosselin G., Imbach J -L; Synthesis of new 2'-deoxy-3'-substituted-α-L-threo-pentofuranonucleosides of thymine as a potential antiviral agents. *Tet Lett* 32(1):79–82 (1991); Genu-Dellac, C., Gosselin G., Imbach J -L, Preparation of new acylated derivatives of L-arabinofuranose and 2-deoxy-L-erythro-pentofuranose as precursors for the synthesis of L-pentofuranosyl nucleosides. 216:240–255 (1991); and Génu-Dellac, C., Gosselin G., Puech F, et al. Systematic synthesis and antiviral evaluation of α-L-arabinofuranosyl and 2'-deoxy-α-L-erythro-pentofuranosyl nucleosides of the five naturally occurring nucleic acid bases. 10(b):1345–1376 (1991).

β-D-Nucleosides and racemic mixtures of synthetic nucleosides can be prepared as described in or by routine modifications or extensions of preparations described in numerous literature references, including but not limited to U.S. Pat. No. 4,916,122 to Chu, et al.; European Patent Application No. 0 217 580; PCT Application No. WO92/10497; Chu, C. K., et al., "A general synthetic method for 2',3'-dideoxynucleosides: total synthetic approach," *Nucleosides & Nucleotides* 8: 5&6, 903–906 (1989); Chu, C. K., et al., "Enantiomeric synthesis of (+)-BCH-189 and (+)-1-β-D-5-(1,3-oxothiolanyl)cytosine from D-mannose and its anti-HIV activity," *J. Org. Chem.* (1991); Chu, C. K., et al., "Structure-activity relationships of pyrimidine nucleosides as antiviral agents for human immunodeficiency virus type 1 in peripheral blood mononuclear cells," *J. Med. Chem.* 32: 612 (1989); Huryn, D. M., et al., "Synthesis of iso-DDA, member of a novel class of anti-HIV agents," *Tetrahedron Lett.* 30:6259–6262 (1989); Kreitsky, T. A. "3'-Amino-2',3'-dideoxyribonucleosides of some pyrimidines: synthesis and biological activities," *J. Med. Chem.* 26: 891–895 (1983); Lin, T., et al., "Synthesis and biological activity of various 3'-azido and 3'-amino analogues of 5-substituted pyrimidine deoxyribonucleosides," *J. Med. Chem.* 26: 1691–1696 (1983); Mansuri, M. M., et al., "Preparation of the geometric isomers of DDC, DDA, D4C and D4T as potential anti-HIV agents," *Bioorg. Med. Chem. Lett.* 1:65–68 (1991); Okabe, M., et al., "Synthesis of the dideoxynucleosides ddC and CNT from glutamic acid, ribonolactone, and pyrimidine bases," *J. Org. Chem.* 53: 4780–4786 (1988); Peterson, M. L., et al., "Synthesis and biological evaluation of 4-purinylpyrrolidine nucleosides," *J. Med. Chem.* 34:2787–2797 (1991); Sterzycki, R. Z., et al., "Synthesis and anti-HIV activity of several 2'-fluoro-containing pyrimidine nucleosides," *J. Med. Chem.* 33:2150–2157 (1990); Wilson, L. J., et al., "A general method for controlling glycosylation stereochemistry in the synthesis of 2'-deoxyribose nucleosides," *Tetrahedron Lett.* 1815 (1990); and Wilson, L. J., et al., "The synthesis and anti-HIV activity of pyrimidine dioxolanyl nucleosides," *Bioorg. Med. Chem. Lett.* 3:2 169–174 (1993).

Stereochomistry at the Phosphorus Atom

Figure 2:
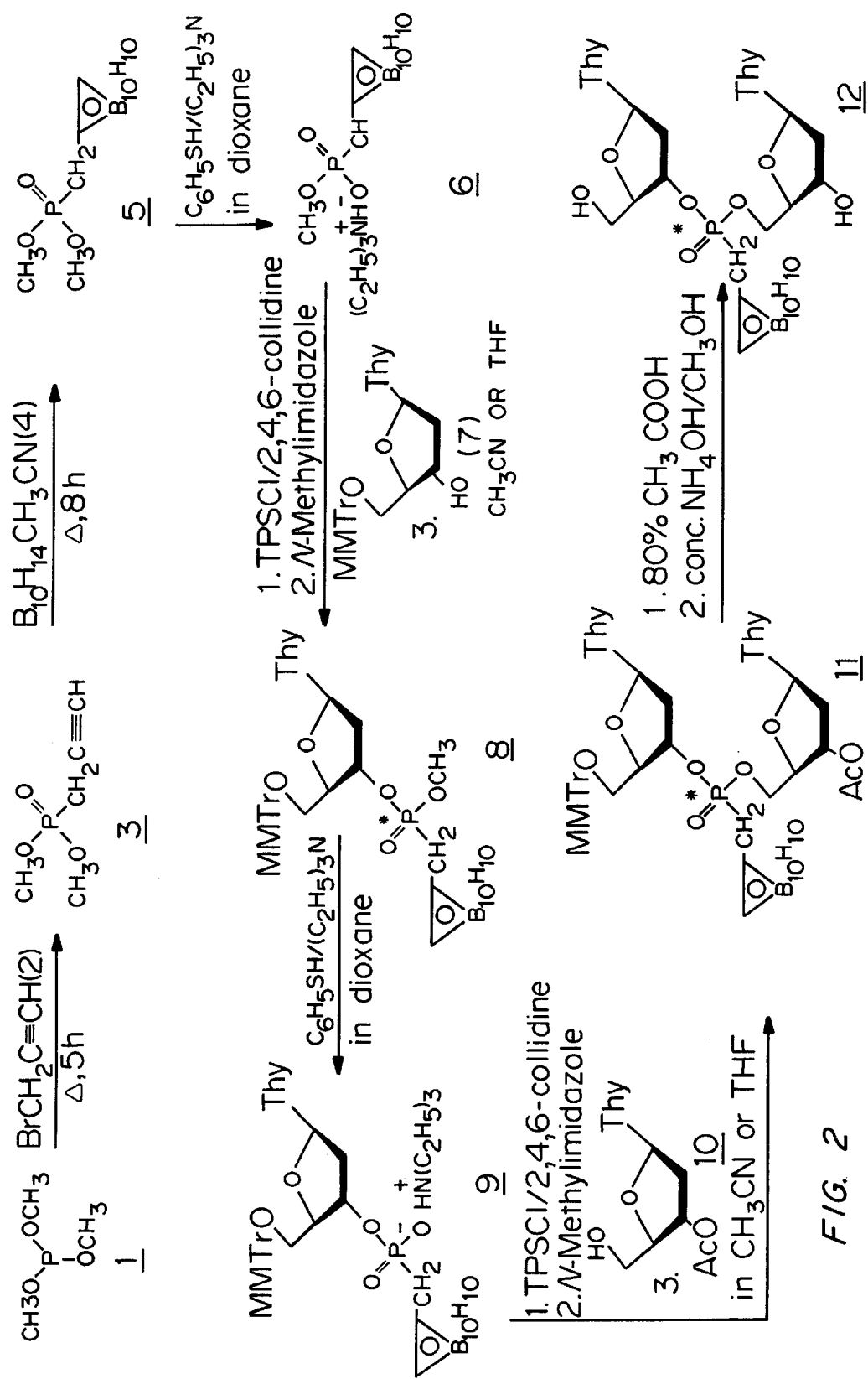
FIG. 2 is a schematic illustration of a process for the preparation of thymidine-(3',5')-thymidine(o-carboran-1-yl) methylphosphonate using the key starting material O-methyl (o-carboran-1-yl)methyl phosphonate.

Replacement of one of the anionic prochiral oxygen atoms of phosphorus with a (carboran-1-yl)methyl moiety generates a center of chirality at the phosphorus atom (see, for example, compound 8, FIG. 2) and in nucleotides and oligonucleotides bearing this moiety (see, for example, compounds 11 and 12, FIG. 2). Due to this modification and the nonstereoselectivity of the coupling reaction described herein, the (carboran-1-yl)methylphosphonate oligonucleotide is typically obtained as a mixture of diastereoisomers.

For a process for the stereocontrolled synthesis of P-chiral oligonucleotides analogues, see Lesnikowski, *Bioorg. Chem.,* 1993, 21, 127–155. Briefly, P-stereodefined, P-chiral oligonucleotides can be prepared using following methods.

(i) Enzymatic Method.

This approach is useful for the stereocontrolled synthesis of phosphorothioate and methylphosphonate oligonucleotide analogues.

(ii) Separation of Diastereoisomeric Oligonucleotides.

This method is most useful for oligonucleotides containing up to three P-chiral internucleotide linkages (eight diastereoisomers).

(iii) Block Synthesis:

A dinucleotide is first synthesized as a mixture of diastereoisomers. In the second step the mixture is separated into individual diastereoisomeric species. Diastereoisomeric dinucleotides are next phosphorylated or phosphitylated and used as synthons in the synthesis of longer oligonucleotides. This method provides a method for the synthesis of oligonucleotides with stereodefined synthetic internucleotide links separated by natural or modified but not stereodefined internucletide links.

(iv) Stereospecific Formation of Internucleotide Linkage:

Diastereoisomerically pure monomers are first synthesized. Using diastereoisomerically pure monomers and a stereospecific coupling reaction P-stereoregular oligomers can be prepared.

(v) Stereospecific Modification of Internucleotide Linkage.

The influence of absolute configuration at phosphorus of P-chiral antisense oligonucleotides on their physicochemical and biochemical properties has been studied. The absolute configuration at the phosphorus atom affects, among other things, solubility, transportability through cellular membranes, affinity toward complementary sequence of target nucleic acid (melting temperature), and resistance towards nucleolytic enzymes (Uhlman, et al., *Chem. Rev.* 1990, 90, 544–584).

II. Methods for the Preparation of Carboranyl-containing Nucleosides and Nucleotides A. Preparation of Nucleosides Containing a 3'—O-[(o-carboran-1-yl-methyl)phosphonate] Moiety and Dinucleotides that Contain a 3',5'-O,O-[(o-carboran-1-yl-methyl)phosphonate] Linkage A novel method is provided for the preparation of nucleosides containing a 3'—O-[(o-carboran-1-yl-methyl)phosphonate] moiety and dinucleotides that contain a 3',5'-O,O-[(o-carboran-1-yl-methyl)phosphonate] linkage. The method involves the use of the key starting material, O-methyl(o-carboran-1-yl)methyl phosphonate, a new and versatile borophosphonylating agent.

As illustrated in FIG. 2, O-methyl(o-carboran-1-yl) methyl phosphonate can be prepared in a three step procedure. In the first step, propargyl bromide is reacted with trimethyl phosphite in a Michaelis-Arbuzuv type reaction to yield O,O -dimethylpropargylphosphonate in good yield. Propargyl bromide can be obtained from Aldrich Chemical Company as a solution in toluene, and toluene is used as the reaction solvent. A range of other solvents can also be used in this step (see, for example, Arbuzov, B. A., Pure Appl. Chem., 1964, 9, 307–335). The reaction can be carried out at any temperature, and for any time period that achieves the desired results. The reaction is usually carried out at a temperature ranging from –20° C. to the boiling temperature of the solvent. It is preferable to limit the access of moisture and oxygen. The reaction time depends upon the structure of the substrate used, the solvent, and the temperature of reaction, and is in general from 1 to 24 hours.

Alkynyl starting materials other that propargyl bromide can be used in this process. Propargyl iodide or propargyl chloride can be substituted for propargyl bromide. As can be surmised by one of ordinary skill in the art given this disclosure, 3-butyn-1-bromide will provide a carboranylethylphosphonate, and 4-pentyn-1-bromide will give carboranylpropylphosphonate. In general, appropriately selected homologs of propargyl bromide can be used to prepare any carboranyl($CH_2$)$_n$P isomer of interest.

In the second step, O,O-dimethylpropargylphosphonate is reacted with decaborane in acetonitrile, according to the general reaction scheme described by Heying et al., *Inor. Chem.* 1963, 1089–1092 to provide O,O-dimethyl(o-carboran-1-yl)methylphosphonate in good yield. The reaction is typically carried out in a Lewis base solvent, e.g., acetonitrile, propionitrile, amine, dialkyl sulfide, cyclic or acyclic ether-(tetrahydrofuran, dioxane, diethyl and diisopropyl ether), or an aromatic solvent as benzene, and for any time period that achieves the desired results. The temperature of reaction generally ranges from room temperature to the boiling temperature of solvent, and the time period of reaction, which depends on the structure of the substrate and reaction conditions, is, in general, from 1 to 24 hours.

The target key starting material O-methyl(o-carboran-1-yl)methyl phosphonate is obtained as a triethylamine salt on demethylation of O,O-dimethyl(o-carboran-1-yl) methylphosphonate using thiophenol and triethylamine in dioxane. A mixture of thiophenol or thiocresol and triethylamine, diisopropylamine or 1,8-diazabicyclo[5.4) undec-7-ene (DBU base) or other organic base in dioxane or other chemically inert solvent can alternatively be used. In another embodiment, 2-mercaptobenzothiazole is used in combination with diisopropylamine (see *Tetrahedron Lett.*, 1988, 29, 5479–5482). In general, a base should be used that forms a salt of O-methyl(o-carboran-1-yl)methyl phosphonate that is soluble in the organic solvent used. While organic bases are preferred, some inorganic counterions may be used, e.g., cesium (obtained from cesium hydroxide).

This method is used in oligonucleotide chemistry to deblock internucleotide linkages protected with an O-methyl group. In contrast, selective demethylation using t-butylamine is only partially successful, as several uncharacterized by-products are obtained. This may be due to partial closo to nido carboranyl transformations.

The key starting material, O,O-dimethyl(o-carboran-1-yl) methylphosphonate, triethylammonium salt, is reacted with a 5'-(and 2'- or base-, if appropriate) protected nucleoside in the presence of triisopropylbenzenesulfonyl-chloride as the activating agent and 2,4,6-collidine and 1-methylimidazole. Triisipropylbenzenesulfonyl chloride is an activating agent which activates the borophosphonylating agent. 2,4,6-Collidine is a scavenger of the hydrochloric acid generated during reaction. 1-Methylimidazole is a nucleophilic catalyst which additionally activates the borophosphonylating agent. Instead of triisipropylbenzenesulfonyl chloride other arylsulfonyl chlorides, or arylsulfonylazolides can be used. In place of 2,4,6-collidine other organic bases can be used, e.g., di(isopropyl)ethylamine. 1-Methylimidazole can be replaced by other nucleophilic catalysts such as 5-chloro-1-ethyl-2-methylimidazole and 5-nitro-1-methylimidazole. The reaction is typically run in an inert organic solvents, such as a cyclic ether as tetrahydrofuran, a nitrile such as acetonitrile, or a chlorocarbon as dimethylchloride at a temperature ranging from –10° C. to boiling temperature of solvent for a time ranging from 5 minutes to 24 hours under anhydrous conditions.

The product of reaction, a 3'—O-[O-methyl-(o-carboran-1-yl-methyl)phosphonated] nucleoside, is demethylated as described above to provide the triethylamine salt of a 3'—O-[(o-carboran-1-yl-methyl)phosphonated] nucleoside.

In an alternative embodiment, if a 5'—O-[(o-carboran-1-yl-methyl)phosphonate] nucleoside is desired, the above steps can be carried out using a 3'- (-and 2'- or base-, if appropriate) protected nucleoside. However, due to the higher chemical activity of the 5'-hydroxyl group, the reaction conditions should be adjusted. Additionally, the solubility of a nucleoside bearing a free 5'-hydroxyl group in general is lower than that with a free 3'-hydroxyl group when the 5'-hydroxyl is protected, and therefore, adjustment of the solvent may be necessary.

The triethylamine salt of the 3'—O-((o-carboran-1-yl-methyl)phosphonated] nucleoside can then be reacted under anhydrous conditions with a 3'-(2'-and base protected, if appropriate) nucleoside to provide a dinucleotide with a 3',5'-O,O-[(o-carboran-1-yl-methyl)phosphonate] linkage. In an alternative embodiment, a 5'-ester can be reacted with a 3'-hydroxyl group of a second nucleoside.

FIG. 2 is a schematic illustration of a process for the preparation of thymidine-(3',5')-thymidine (o-carboran-1-yl) methylphosphonate using the key starting material O-methyl (o-carboran-1-yl)methyl phosphonate. The process is described in detail in Example 2. Column chromatography was performed on silica gel 60, 230–400 mesh from Aldrich (Milwaukee, Wis.). Thin layer chromatography was performed on silica gel F 254 plates from Sigma (St. Louis, Mo.). Solvents were purchased in the highest available quality and used without drying. Mass spectra were recorded on a VG 70-S or Perkin-Elmer Sciex API-3 spectrometer. $^{31}$P NMR spectra were recorded on a Bruker WP-200 spectrometer operating at 81.0 MHz with 85% $H_3PO_4$ used as an external standard. $^1$H and $^{13}$C NMR spectra were recorded on a GE QE Plus spectrometer operating at 300.15 MHz and 75.48 MHz, respectively, with tetramethylsilane as the external standard. Shifts downfield from the standard were assigned as positive. uv spectra were recorded on a Beckman DU-65 spectrophotometer. Reversed phase high performance liquid chromatography (RP-HPLC) was performed on a Hewlett-Packard 1050 system using a Whatman Partisphere C18 5 μm, 4.7×235 mm column.

EXAMPLE 2

Preparation of thymidine-(3',5')-thymidine (o-carboran-1-yl)methylphosphonate

O,O-Dimethylpropargylphosphonate (3). Propargyl bromide (2, FIG. 2) [0.15 mol, 22.3 g of 80% solution in toluene], and trimethylphosphite (1) (0.19 mol, 23.6, 25% molar excess) were stirred under reflux for 5 hours, and then distilled. The low boiling fractions consisted mainly of unreacted 2 and O,O-dimethylmethylphosphonate as a main by-product. The fraction boiling at 50–67° C./0.5 mm Hg was collected and redistilled yielding 3. Bp 69–91° C./1 mm Hg (9.5 g, 45%). $^{31}$P NMR (CDCl$_3$): δ 21.0, $^1$H NMR (CDCl$_3$): δ0 2.8 (dd, 2H, $J_{PH}$=18.4 Hz, $J_{HH3}$=2.5 Hz, PCH$_2$), 3.8 (d, 1H, $J_{PH}$=9.5 Hz, CH), 3.9 (d, 6H, $J_{pH}$=13.8 Hz, CH$_3$OP), $^{13}$C NMR (CDCl$_3$): δ 16.0 (d, $J_{PC}$=145.8 Hz, PCH$_2$), 53.0 (d, $J_{PC}$=6.8 Hz, CH$_3$OP). 71.2 (d, $J_{PC}$=10.6, CH), 73.4 (d, $J_{PC}$=14.3. CH$_2$C).

O,O-Dimethyl(o-carboran-1-yl)methylphosphonate (5). Method A. Decaborane (4) (0.01 mol, 1.2 g) was dissolved in dry CH$_3$CN (20 mL) and the resulting solution was heated under reflux. After 15 minutes, 3 (0.02 mol, 2.8 g) was added to the boiling solution,and heating continued for 8 hours. The reaction mixture was left overnight at room temperature and then filtered. The solvent was evaporated under reduced pressure and the oily ID residue was redissolved in CH$_2$Cl$_2$ (25 mL). The resulting solution was washed with H$_2$O (3×20 mL) and the organic phase was dried over MgSO$_4$ and evaporated. The oily residue was redissolved in CH$_2$Cl$_2$ (20 mL), and then precipitated with hexanes (250 mL). The precipitate was filtered and hexanes evaporated under reduced pressure to provide an oily residue which crystallized spontaneously. The crystals were washed with hexanes and dried under reduced pressure. For analysis, the resultant product was recrystallized from hexanes (yield 1.1 g, 40%).

Method B. Decaborane (4) (0.02 mol, 2.4 g) was dissolved in dry toluene (350 mL) and then propionitrile (0.34 mol, 18.7 g) was added. The resulting solution was heated under reflux for 15 minutes and then 3 (0.017 mol, 4.5 g) was added. The solution was heated under reflux for five hours, and then the reaction mixture was left overnight at room temperature. Product 5 was isolated as described in Method A; yield 1.6 g, 36%. Fine white flakes, mp 68–70° C.; anal. calcd. for C$_5$H$_{19}$PO$_3$B$_{10}$: C, 22.55: H, 7.19. Found: C, 22.74; H, 7.21; $^{31}$P NMR (CDCl$_3$) δ 20.7; $^1$H NMR (CDCl$_3$) δ 0.8–3.4 (b signal, 10H, CCHB$_{10}$H$_{10}$) 2.8 (d, 2H, $J_{PH}$=20.3 Hz, PCH$_2$), 3.7 (d, 6H, $J_{PH}$=10.2 Hz, CH$_3$OP), 4.4 (b s, 1H, CH); $^{13}$C NMR (CDCl$_3$, δ 33.2 (d, $J_{PC}$=144.2 Hz, PCH$_2$), 53.0 (d, $J_{PC}$=6.8 Hz, CH$_3$OP), 59.84 and 67.3 (s and s, CCHB$_{10}$H$_{10}$).

O-Methyl(o-carboran-1-yl)methylphosphonate, Et$_3$N salt, (6). Compound 5 (0.66 g, 2.5 mmol) was dissolved in dioxane (5 mL), and thiophenol (10 mL) and triethylamine (10 mL) were added. After two hours at room temperature, the reaction mixture was evaporated and the oily residue dissolved in CH$_2$Cl$_2$ and triturated with hexanes, then centrifuged to remove insoluble impurities. The hexanes were evaporated, yielding 6 as an oil which crystallized on cooling. The yield of crude product 6, which contained traces of thiophenol, was 0.7 g (79%). Crude 6 can be used directly for the synthesis of 8. For analytical purposes, 6 was purified by means of silica gel chromatography using 0-50% CH$_3$OH in CH$_2$Cl$_2$ as eluent. $^{31}$P NMR (CDCl$_3$) δ 14.8: $^1$H NMR (CDCl$_3$); δ 1.3 (t, 9H, $J_{HH}$=7.4 Hz, CH$_3$), 1.0–3.1 (b signal,10H. CCHB$_{10}$H$_{10}$), 2.6 (d, 2H, $J_{PH}$=18.4 Hz, PCH$_2$), 3.0–3.1 (m, 6H, NCH$_2$), 3.6 (d, 6H, $J_{PH}$=9.2 Hz, CH$_3$OP), 4.7 (b S, 1H, CH); $^{13}$C NMR (CDCl$_3$) δ 8.52 (s, CH$_3$CH$_2$N), 34.20 (d, $J_{PC}$=133.0 Hz, PCH$_2$), 45.77 (S, CH$_3$CH$_2$N), 52.00 (d, $J_{PC}$=5.9 Hz, CH$_3$OP), 60.38 and 70.00 (s and s, CCHB$_{10}$H$_{10}$).

5'—O-Monomethoxytritylthymidine 3'—O-[O-methyl (o-car-boran-1-yl)methylphosphonate] (8). Compound 6 (0.2 g, ca. 0.6 mmol) and triisopropylbenzenesulfonyl-chloride (0.3 g, 1.0 mmol) were dissolved in dry THF (1.0 mL) and then 2,4,6-collidine (0.13 mL, 1.0 mmol) was added with stirring. After 15 minutes at room temperature, 5'—O-monomethoxytritylthymidine 7 (0.15 g, 0.3 mmol) dissolved in dry THF (0.3 mL) was added, followed by 1-methylimidazole (0.1 mL, 2.0 mmol). After 2 hours at room temperature, the reaction mixture was evaporated to dryness. The residue was dissolved in CH$_2$Cl$_2$ (5 mL). The resultant solution was washed with H$_2$O (3×5 mL). The organic fraction was dried over MgSO$_4$ and evaporated to dryness. The crude product was purified by silica gel column chromatography using a stepwise 0-2% gradient of CH$_3$OH in CH$_2$Cl$_2$ as eluent. Fractions containing 8 were collected, and the organic solvents evaporated to dryness. The residue was dissolved in CH$_2$Cl$_2$ and precipitated from hexanes. The precipitate was dried under vacuum yielding 8 as a mixture of two diastereoisomers (0.1 g, 44%). TLC R$_f$ 0.30 and 0.37 (94:6 CH$_2$Cl$_2$—CH$_3$OH); UV (95% C$_2$H$_5$OH) λ 265.7 nm, λ$^{min}$, 250.0 nm, λ230.0 nm: $^{31}$P (CDCl$_3$) δ 33.0: $^1$H NMR (CDCl$_3$) δ 1.2 (S, 3H, CH$_3$(5)], 0.9–3.1 (b signal, 1OH, CCHB$_{10}$H$_{10}$), 2.3–2.6 (m and m, 2H, H$_2$'), 2.7 and 2.8 (d and d, 2H, $J_{PH}$=18.4 Hz, PCH$_2$), 3.4 and 4.2 (d and d, 2H, $J_{HH}$=9.0, H5'), 3.6 and 3.7 (d and d, 3H, $J_{PH}$=9.0 Hz, CH$_3$OP), 3.5–3.6 (m, 1H, H4'), 3.8 (S, 3H, CH$_3$OPh), 4.3 and 4.4 (b s and s,1H, CH), 5.1 (b m, 1H, H3'), 6.4 (t, 1H, $J_{HH}$=4.5 Hz, H1'), 7.8–7.9 and 7.2–7.4 (m and m, 14H, arom.), 7.5 and 7.6 (s and s, 1H, H6), 8.5 and 8.6 (s and s, 1H, H3); $^{13}$C NMR (CDCl$_3$) δ 11.71 [S, CH$_3$(5)], 35.03 (S, C2'), 39.25 (d, PCH$_2$, $J_{PC}$=34.6), 53.26 (d, CH$_3$OP, $J_{PC}$=5.1 Hz, ), 55.17 (S, CH$_3$OPh), 59.74 (s, C5'), 63.06 (C3'), 62.86 and 66.56 (s and s, CCHB$_{10}$H$_{10}$), 84.25 and 84.59 (s and s, C1'), 87.46 and 87.53 (s and S, C4'), 113.29 and 113.32 (S and s, C5), 127.40, 128.03, 128.18, 128.23, 130.24, 136.77, 143.34, 158.88 (singlets, arom.), 134.32 and 134.38 (s and s, C6), 150.14 and 150.77 (s and s, C2), 163.28 (s, C4).

5'-O-Monomethoxytritylthymidine-3'-O-(o-car-boran-1-yl)methylphosphonate, Et$_3$N salt (9). Compound 8 (40 mg, 0.05 mmol) was dissolved in dioxane (0.1 mL), and thiophenol (0.2 mL) and triethylamine (0.2 mL) were added. After 5 minutes at room temperature, the reaction mixture was precipitated with diethyl ether and centrifuged to remove insoluble impurities. The ether supernatant containing product was evaporated to dryness, and the residue dissolved in CH$_2$Cl$_2$ and precipitated twice with hexanes. The yield of chromatographically homogeneous 9 was 29 mg (70%). TLC $R_f$ 0.08 (9:1 $CH_2Cl_2$—$CH_3OH$) 0.54 (9:1 $CH_3CN$—$H_2O$); UV (95% $C_2H_5OH$) $\lambda_{max}$267.0 nm, $\lambda_{min}$ 244.2 nm; $^{31}P$ NMR ($CDCl_3$) δ 12.85; $^1H$ NMR ($CDCl_3$) δ 1.3 (t, 9H, $J_{HH}$=7.3 Hz, $CH_3$), 1.4 [s, 3H, $CH_3(5)$], 0.6–3.2 (b signal, 10H, $CCHB_{10}H_{10}$), 2.5 (d, 2H, $J_{PH}$=18.4 Hz, $PCH_2$, 2.9–3.1 (m, 6H, $NCH_2$), 3.3 and 3.5 (d and d, 2H, $J_{HH}$=9.0, H5'), 3.8 (s, 3H, $CH_3OPh$), 4.1 (b S, 1H, H4'), 4.8 (b t, 1H, H3'), 4.9 (b s, 1H, CH), 6.4 (m, 1H, 1H'), 6.9 and 7.1–7.4 (d and m, 14H, arom.), 7.6 (s, 1H, H6), 9.3 (S, 1H, H3); $^{13}C$ NMR ($CDCl_3$) δ 8.54 (S, $CH_3CH_2N$), 11.70 [s, $CH_3(5)$], 36.50 (d, $J_{PC}$=102.0 Hz, $PCH_2$), 40.05 (s, C2'), 45.66 (s, $CH3CH_2N$), 55.23 (s, $CH_3OPh$), 60.34 (s, C5'), 76.24 (C3'), 70.05 and 75.65 (s and s, $CCHB_{10}H_{10}$), 84.55 (s, C1'), 87.23 (s, C4'), 113.31 (s, C5), 127.10, 127.31, 127.83, 128.00, 128.35, 128.41, 129.20, 134.00, 135.50, 144.45, 157.25 (singlets. arom.). 130.38 (s, C6), 151.05 (s, C2), 164.05 (s, C4).

5'-O-Monomethoxytritylthymidine(3',5')3'-O-acetylthymidine(o-carboran-1-yl)methylphosphonate (11). Compound 9 (16 mg, 0.02 mmol) and triisopropylbenzenesulfonyl chloride (8 mg, 0.025 mmol) were dissolved in dry $CH_3CN$ (0.2 mL), and 2,4,6-collidine (5 μl, 0.035 mmol) was added with stirring. After 15 minutes at room temperature, a solution of 3'-O-acetylthymidine (10) (10 mg, 0.035 mmol) in dry $CH_3CN$ (0.05 mL) followed by 1-methylimidazole (2 μL, 0.025 mmol) were added to the mixture. The mixture was left overnight at room temperature and then $CH_2Cl_2$ (1 mL) was added. The resultant solution was washed with water (4×0.5 mL), and the organic layer separated, dried over $MgSO_4$, and evaporated to dryness. The crude product was purified by silica-gel column chromatography using a stepwise 0-3% gradient of $CH_3OH$ in $CHCl_2$ as eluent. Fractions containing 11 were collected and the organic solvents evaporated to dryness. The residue was dissolved in dichloromethane and precipitated from hexanes. The resultant precipitant was dried under vacuum yielding 11, yield 6 mg, 30%. TLC $R_f$ 0.56 (9:1 $CH_2Cl_2$—$CH_3OH$), UV (95% $C_2H_5OH$) $\lambda_{max}$, 265.0 $\lambda_{min}$ 245.0 nm, $\lambda_{sh}$ 229.0 nm; $MS/LSI(FAB^+)$ 1016 [M +2Li]; $^{31}P$ NMR ($CDCl_3$) δ 21.16 and 22.95; $^1H$ NMR ($CDCl_3$) δ 1.23 [d, 3H, $J_{HH}$6=3 Hz, $CH_3(5)$], 1.44 [s, 3H, $CH_3(5)$], 1.50–1.72 and 2.24–2.48 (b m and b m, 2H and 2H, H2'), 0.6–3.2 (b signal, 10H, $CCHB_{10}H_{10}$), 1.88 (d, $J_{PH}$=8.5 Hz, 2H, $PCH_2$), 2.07 (s, 3H, $CH_3CO$), 3.35–3.58 (m, 2H, H5'), 3.78 (s, 3H, $CH_3OPh$), 3.85–4.4 (mm, 4H, H5' and H4'), 5.0 (b s, 1H, CH), 5.10–5.25 (b m, 1H, H3'), 6.0–6.4 (b mm, 3H, H3', H1'), 6.70–6.85 and 7.10–7.50 (14H. arom.). Thymidine(3', 5')thymidine(o-carboran-1-yl)methylphosphonate (12). Compound 11 (4.5 mg, 4.5 μmol) was dissolved in $CH_3OH$ (0.15 mL), concentrated $NH_4OH$ (25%, $NH_3$) was added (0.15 mL), and the reaction mixture maintained at room temperature for 30 minutes (TLC monitoring, solvent system 9:1 $CH_2Cl_2$—$CH_3OH$). The solvent was evaporated to dryness yielding 5'-O-monomethoxytrityl-thymidine(3',5') thymidine (o-carboran-1-yl)methylphosphonate as a white solid [TLC $R_f$ 0.44 (9:1 $CH_2Cl_2$—$CH_3OH$)]. Crude 5'-O-monomethoxytrityl-thymidine(3',5')thymidine-o-carboran-1-yl)methylphosphonate (=4.5 μmol) was dissolved in 80% acetic acid (0.5 mL) and heated at 60° C. After approximately 30 minutes (TLC monitoring, 9:1 $CH_2Cl_2$:$CH_3OH$) acetic acid was coevaporated with n-butyl alcohol. The crude product was dissolved in pyridine-$CH_2Cl_2$ and after precipitation with hexanes purified by silica gel column chromatography, using a stepwise 0-10% gradient of $CH_3OH$ in $CH_2Cl_2$ as eluent. Compound 12, isolated as a mixture of two diastereoisomers, was then dissolved in water and lyophilized. The yield was 2.1 mg (70%). TLC $R_f$ 0.14 (9:1 $CH_2Cl_2$—$CH_3OH$), 0.32 and 0.38 (85:15 $CH_2Cl_2$—$CH_3OH$); UV (95% $C_2H_5OH$) $\lambda_{max}$ 266.0 nm, $\lambda_{min}$ 235.0 nm, HPLC (gradient from 5% to 50% $CH_3CN$ in 0.05 M triethylammonium acetate (TEAA) (pH=7.0) during 40 min, 1.0 Ml/min) 12-fast $R_t$=20.5 min and 21.5 min, 12-slow $R_t$=33.9 min and 35.5 min. MS(FAB') 12-fast 676.7[M-B], $MS(FAB^+)$12-slow 725.6 [M+K].

B. Synthesis of Oligonucleotide Bearing 3',5'-[O-(o-carboran-1-yl)alkyl]phosphates, [S-(o-carboran-1-yl)alkyl] phosphorothioates, or [Se-(o-carboran-1-yl)alkyl] Phosphoroselenoates Internucleotide Linkage.

Figure 3:
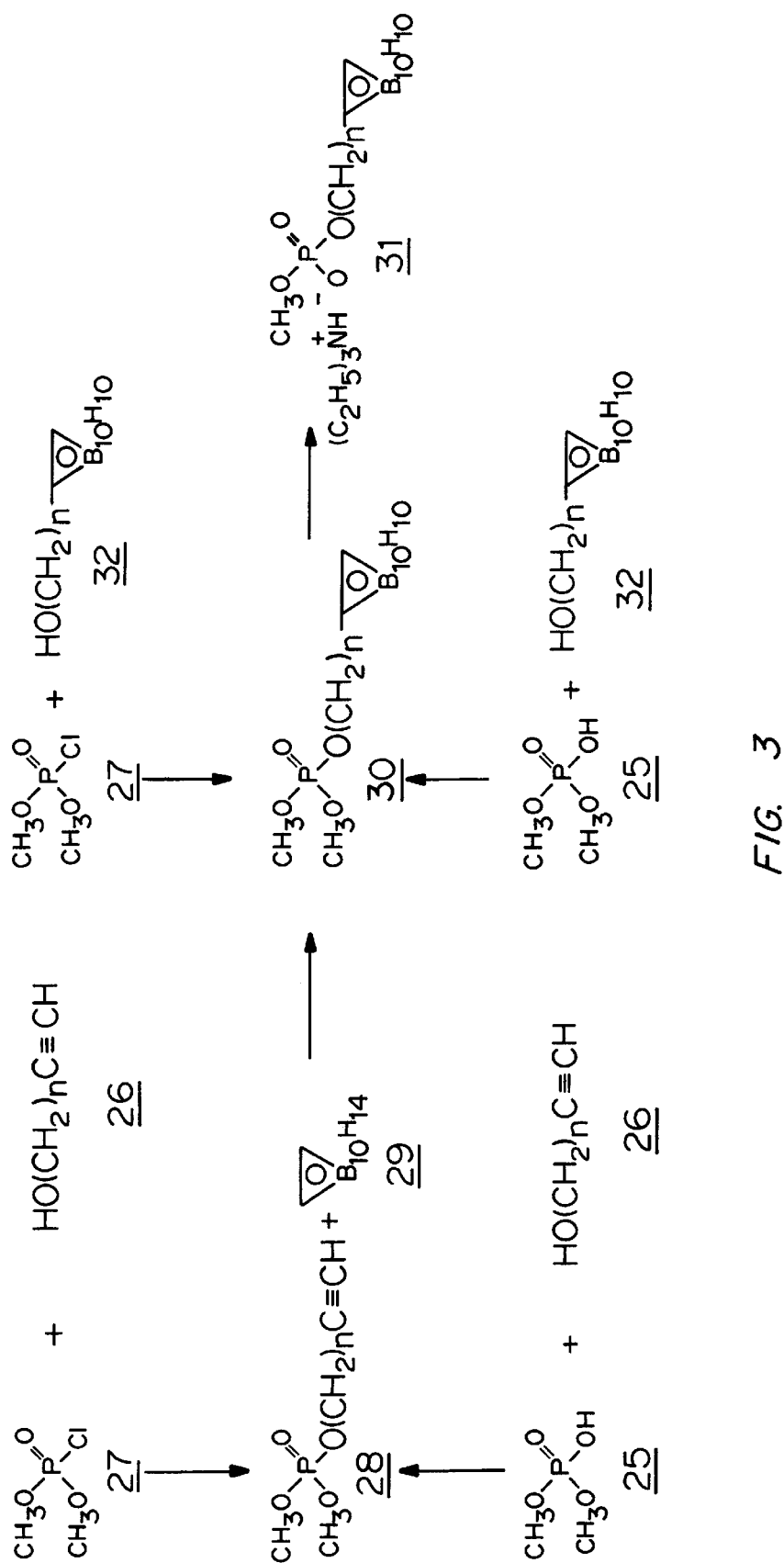
FIG. 3 is an illustration of a process for the preparation of O-methyl-[O-(o-carboran-1-yl)alkyl]phosphate.

Oligonucleotides bearing a 3',5'-[O-(carboran-1-yl)alkyl] phosphate, [S-(carboran-1-yl)alkyl]phosphorothioate, or (Se-(carboran-1-yl)alkyl)phosphoroselenoate internucleotide linkage can be conveniently synthesized using a suitable monomer such as 5'-O-monomethoxytritylnucleoside 3'-[O-(carboran-1-yl)-alkyl]phosphate, [S-(carboran-1-yl) alkyl]phosphorothioate or [Se-(carboran-1-yl)alkyl] phosphoroselenoate as described previously for the oligonucleotides containing 3',5'-[(o-carboran-1-yl)alkyl] phosphonate internucleotide linkage as illustrated in FIG. 3. As known to those skilled in the art, many other groups can be used to protect the 5'-position, for example, dimethoxytrityl. The term (carboran-1-yl)alkyl refers to (o-carboran-1-yl)(lower alkyl), and in particular, (o-carboran-1-yl)(lower linear alkyl).

The monomers are prepared by the reaction of a suitably protected nucleoside with a series of new borophosphorylating agents type of O-methyl-[O-(carboran-1-yl)alkyl] phosphate (31), O-methyl-[S-(o-carboran-1-yl)alkyl] phosphorothioate (36), and O-methyl-[Se-(o-carboran-1-yl) alkyl]phosphoroselenoate (41) followed by the demethylation of the fully protected intermediates 30, 35, and 40 respectively, as described for synthesis of [O-methyl-(o-carboran-1-yl)alkyl]phosphonate previously.

The borophosphorylation reaction (synthesis of the specific monomer) proceeds under the conditions described for 5'-0-monomethoxytritylnucleoside 3'-O-methyl-(O-(o-carboran-1-yl)alkyllphosphonate however the reaction conditions (activating agent, nucleophilic catalyst, solvent, temperature and reaction time) are adjusted in light of the substrates used.

Borophosphorylating agents type of O-methyl-[O-(o-carboran-1-yl)alkyl]phosphate (31), O-methyl-[S-(o-carboran-1-yl)alkyl]phosphorothioate (36), and O-methyl-[Se-(o-carboran-1-yl)alkyl]phosphoroselenoate (41) are prepared as follows:

O-Methyl-fO-(o-carboran-1-yl)alkylphosphate (31).
O-Dimethylphosphate (25) is reacted with a suitable alcohol of the formula (n-1)-alkyn-1-ol (26) (where n=number of carbon atoms in linear hydrocarbon chain, also branched alkynes can be used) in the presence of a suitable activating agent yielding O,O-dimethyl-(O-alkynyl)phosphate (28). Another approach to intermediate 28 is based on the reaction of O,O-dimethylchlorophosphate (27) with alcohol (26) in pyridine or other proper solvent. Both reactions are performed according to well known methods of phosphorylation [Methoden der organische Chemie, Organische Phosphor-Verbindungen (Houben-Weyl), Band XII/1 and XII/2, George Thieme Verlag, Stuttgart, 1964; also as above Band E1 and E2, 1982). The reaction of 28 with decaborane (29) and selective demethylation (removing one of methyl groups) of intermediate O,O-dimethyl-[O-(carboran-1-yl)alkyl] phosphate (30), leading to (31) can be performed as described for the synthesis of O-methyl-[(o-carboran-1-yl)alkyl]phosphonate. Another approach to (30) is based on reaction of O,O-dimethylphosphate (25) or O,O-dimethylchlorophosphate (27) with (o-carboran-1-yl)alkylol (32) as described above. (o-Carboran-1-yl) alkylol (32) can be prepared in the reaction of hydroxyl protected alkynol with dodecaborane followed by deprotection of hydroxyl function.

O-Methyl-[S— (o-carboran-1-yl)alkyl]phosphorothioate (36). Several approaches can be used to prepare the title compound. The simplest is the alkylation reaction between O,O-dimethylphosphorothioate (33) and suitable (n–1)-alkyn-1-bromide (34) (n=number of atoms in hydrocarbon chain; linear as well as branched alkynes could be used, as well as chloride or iodide derivative), followed by the reaction with dodecaborane and selective removing of one of methyl groups (Methoden der Organische Chemie, Organische Phosphor-Verbindungen (Houben-Weyl), Band XII/1 and XII/2, George Thieme Verlag, Stuttgart, 1964; also as above Band E1 and E2, 1982).

O-Methyl-[Se-(o-carboran-1-yl)alkyl] phosphoroselenoate (41). The title compound can be prepared as described for O-methyl-[S-(o-carboran-1-yl)alkyl] phosphorothioate (36) except that O,O-dimethylphosphoroselenoate (38) is used. Another method is based on the reaction of O,O,Se-trimethylphosphoroselenoate (39) with suitable (n–1)alkyn-1-bromide (34) followed by the reaction with dodecaborane (29) or directly with [(o-carboran-1-yl)alkyl]bromide (37), followed by selective removal one of the methyl group. The second method could be used also for 36 synthesis.

C. Preparation of Oligonucleotides That Contain a 3',5'-O,O-[(carboran-1-yl-methyl)phosphonate] Linkage A dinucleotide containing a 3',5'-O,O-((carboran-1-yl-methyl)phosphonate] linkage, after selective deprotection and phosphitylation of its 3'-end with 2-cyanoethyl-N,N-diisopropylchlorophosphoramidite, can be used as a building block for the synthesis of longer oligonucleotides bearing one or more alternating (carboran-1-yl) methylphosphonate linkages by automatic synthesis on solid support. See, for example, Applied Biosystems User Bulletin No. 43 1987, Applied Biosystems, Foster City, Calif. Oligonucleotides that include one or more 3',5'-O,O-[(carboran-1-yl-methyl)phosphonate) linkages can also be prepared using solution techniques as known to those skilled in the art.

Natural oligonucleotides are synthesized enzymatically on a small scale routinely. Modified oligonucleotides can be also prepared using enzymes (see Lesnikowski, Z. J., Bioorganic Chem, 1993, 21, 127–155). Enzymatic synthesis of (carboranyl-1-methyl)phosphonate oligonucleotides can be carried out as a modification of the enzymatic synthesis of methylphosphonate oligonucleotide analogues (see Lesnikowski above).

D. Preparation of Oligonucleotides That Contain Carboranyl-Containing Base Units As described in the Background of the Invention, nucleosides with a carboranyl moiety in the base unit have been previously reported. However, it is believed that this is the first disclosure of oligonucleotides that include one or more nucleosides with carboranyl moieties in selected base units. It has been surprisingly discovered that, while useful oligonucleotides can be prepared that contain a carboranyl-containing base in any of the nucleosides, it is preferred that the carboranyl-containing base be located at the 3' or 5'-terminus or in the nucleoside adjacent to the 3' or 5'-terminal nucleoside, or in some combination thereof.

Methods for the automated production of oligonucleotides are described above. Given the disclosure herein, one of ordinary skill in the art will know how to prepare a wide variety of oligonucleotides with carboranyl-containing base units for a diverse range of applications, all of which are intended to fall within the scope of this invention. oligonucleotides that contain one or more carboranyl-containing bases can also be prepared using solution techniques as known to those skilled in the art.

Example 3 provides a detailed description for the preparation of an oligonucleotide that contains twelve thymine residues, wherein one or more or the thymidine bases contain carboranyl moieties in the 5-position. Example 4 provides detailed physical characterization of the oligonucleotides prepared in Example 3. These examples are merely illustrative, and not intended to limit the scope of the invention.

EXAMPLE 3

Preparation of Dodecathymidylate Containing 5-(o-carboran-1-yl)-2'-O-deoxyuridine 5'-o-Dimethoxytritylthymidine 3'-(N,N-diisopropyl-2-cyanoethyl)phosphoramidite was obtained from Chem-Impex International (Wood Dale, Ill., lot No. 105198). Thymidine loaded 1 $\mu$M CPG (500 Å pore size) columns were purchased from Applied Biosystems (Foster City, Calif.).

5-(o-Carboran-1-yl)-2'-O-deoxyuridine (CDU) (13, see FIG. 4). 5-(o-Carboran-1-yl)-2'-o-deoxyuridine (CDU) (compound 13, FIG. 4) was obtained from 5-iodo-2'-O-deoxyuridine in a five steps procedure, as described in detail by Yamamoto, Y., Seko, T., Rong, F. G., Nemoto, H., Tetrahedron Lett., 1989, 30, 7191–7194.

5-(o-Carboran-1-yl)-5'-O-dimethoxytrityl-2'-O-deoxyuridine (14). After 3 coevaporations with anhydrous pyridine, CDU (400 mg, 1.08 mmol) was dissolved in anhydrous pyridine (10 mL) under an argon atmosphere. To the stirring solution was added 4,4'-dimethoxytritylchloride (457 mg, 1.35 mmol, 1.25 eq.). After stirring for 6 hours at room temperature under argon, the reaction was quenched with 1 mL of methanol, then diluted with $CH_2Cl_2$ (30 mL). The mixture was washed with a saturated solution of $NaHCO_3$ (25 mL) and then with water (2×25 mL). The organic layer was extracted, dried over $Na_2SO_{41}$ filtered, and then evaporated under reduced vacuum, and coevaporated with toluene. The residual foam was dissolved in $CH_2Cl_2$ and applied to a silica gel column. A gradient of from 0% to 5% $CH_3OH$ in $CH_2Cl_2$ was used as the eluent. The fractions containing the desired-product were combined, the solvent was evaporated under vacuum, and then the residue was precipitated in n-hexane to provide 5'-O-dimethoxytrityl-CDU as a white powder (497 mg, 68% yield). $^1$H NMR ($CDCl_3$) $\delta$ 7.81 (S, 1H, NH); 7.51–7.319 (m, 10H, H-6 and 9H-arom.); 6.96 (m, 4H, H in a of $OCH_3$); 6.23 (t, 1H, H-1'); 5.78 (bs, 1H, H-carboranyl); 4.50 (m, 1H, H-3'); 4.21 (m, 1H, H-4'); 3.90 (s, 6H, 2x$OC\underline{H}_3$); 3.60 (m, 1H, H-5'(H-5")); 3.35 (dd, 1H, H-5" (H-5'); 3.12 (d, 1H exch, OH-3'); 3.2–1.2 (bm, 10H, H of $B_{10}H_{10}$); 2.61 (m, 1H, H-2'(H-2")); 2.15 (m, 1H, H-2" (H-2').

Figure 4:
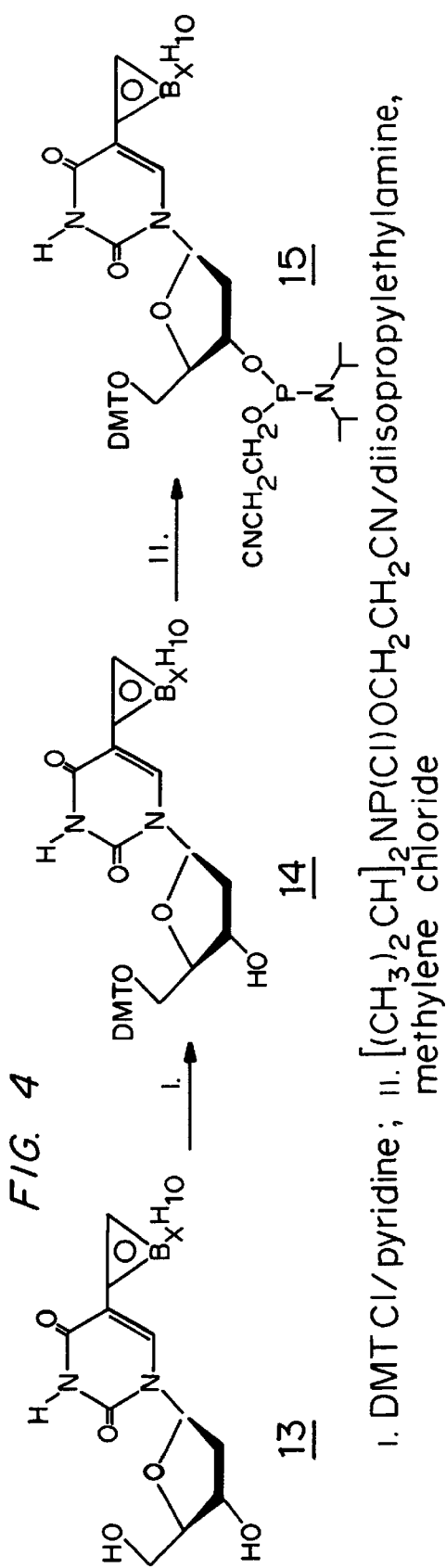
FIG. 4 is an illustration of a process for the preparation of 5-(o-carboranyl)-s'—O-dimethoxytrityl-2'—O-deoxyuridine-3'-(N,N-diisopropyl-B-cyanoethyl) phosphoramidite.
Figure 5:
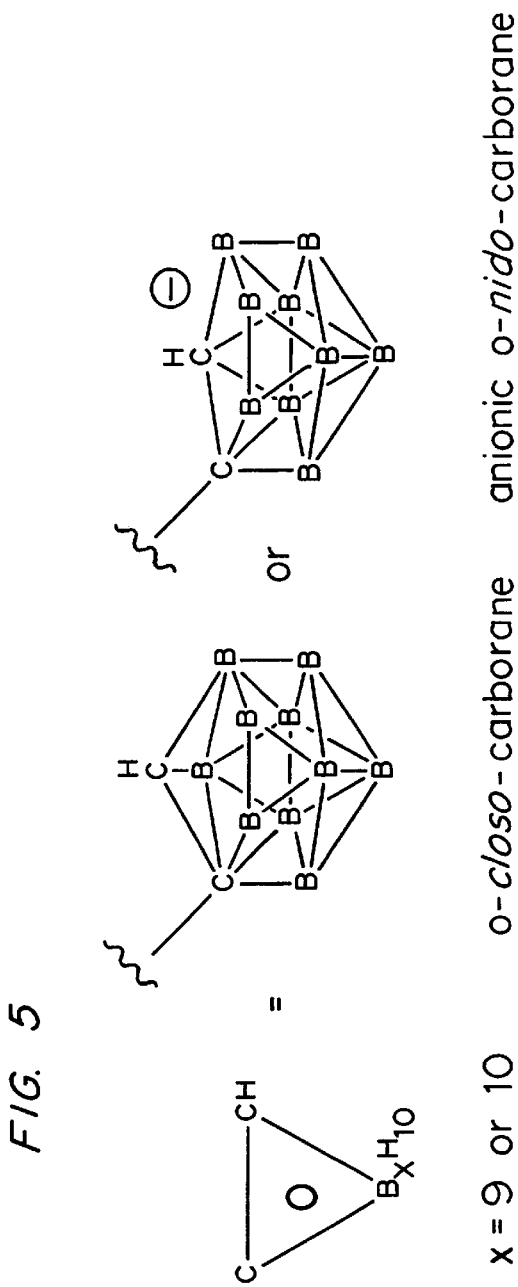
FIG. 5 is an illustration of the chemical structures of a $B_xH_{10}$ carborane moiety and the anionic o-nido-7, 8-$C_2B_9H_{(11,12)}$ and o-closo-1,2-$C_2B_{10}H_{12}$ forms of carborane.

5-(O-Carboran-1-yl)-5 '-O-dimethoxytrityl-2'-O-deoxyuridine-3'-[N,N-diisopropyl-$\beta$-cyanoethylphosphoramidite] (15, see FIG. 4). Compound 14 (200 mg, 0.297 mmol) was dissolved in freshly distilled anhydrous $CH_2Cl_2$ (1.2 mL). After stirring under an argon atmosphere for 5 minutes, diisopropylethylamine (DIEA, 207 μL, 1.19 mmol, 4 eq.) was added dropwise under argon followed by the addition of the phosphitylating agent, 2-cyanoethyl N,N-diisopropylaminochlorophosphine (100 μL, 0.445 mmol, 1.5 eq.). The reaction was monitored by TLC using n-hexane-EtOAc-NEt$_3$ 50:49:1. After stirring for 1 hour under argon at room temperature, excess of phosphitylating reagent was added (20 μL, 0.089 mmol) and the reaction was allowed continue for 30 minutes. The mixture was then diluted with ethyl acetate freshly passed through Al$_2$O$_3$ (10 mL), and poured into a brine solution (6 mL). The organic layer was washed two more times with brine (2×6 mL), dried over Na$_2$SO$_4$, filtered, and evaporated to dryness under vacuum. The residual oil was then dried under high vacuum to remove excess diisopropylethylamine, producing a white foam. Purification of the crude material was carried out on silica gel column chromatography using N-hexane-EtOAc-NEt$_3$ as eluent at the ratio 90:9:1 to 20:79:1. Appropriate fractions containing 3'-phosphoramidite CDU as a diastereoisomer mixture were combined and evaporated under vacuum. The desired compound 15 was then precipitated in cooled n-hexane at −20° C. and the pellet dried further under high vacuum for 20 hours (217.7 mg, 84% yield). $^{31}$P NMR (CDCl$_3$) δ 149.90 and 149.61 ppm. $^{1}$H NMR (CDCl$_3$) δ 7.99 (s, 1H, NH); 7.74–7.17 (m, 10H, H-6 and H-arom.); 6.81 (m, 4H; H in a of OCH$_3$); 6.11 (m, 1H, H-1'); 5.65 (bs, 1H, H-carboranyl); 4.48 (m, 1H, H-3'); 4.22 (m, 1H, H-4'); 4.13 (m, 1H, H-5'(H-5")); 3.77 (2s, 6H, 2OCH$_3$); 3.74–3.19 (m, 5H, H-5', H-2' and H-2", 2×H of NC$\underline{H}$(CH$_3$)$_2$); 2.72 (t, 1H, H of POC $\underline{H}_2$CH$_2$CN)2.58 (t, 2H, H of POCH$_2$C$\underline{H}_2$CN); 2.42 (t, 1H, H of POC$\underline{H}_2$CH$_2$CN); 3.2–1(bm, 10H, H of B$_{10}$H$_{10}$); 1.2 (sev d, 12H, H of NCH(C$\underline{H}_3$)$_2$).

Automatic synthesis of CDU containing dodecathymidylate (19–24) and unmodified d(T)$_{12}$ (18), and d(A)$_{12}$ (19). Dodecathymidylic acid analogues bearing one or two 5-(o-carboran-1-yl)uracil residues at 1st (compound 19), 2nd (compound 20), 7th (compound 21), 11th (compound 22) and both, 10th and 11th (compound 23), and 1st and 11th (compound 24) location of the twelvemer 18 (see Table 1) were obtained by solid phase automatic synthesis using a standard β-cyanoethyl cycle (see, for example, Applied Biosystems USER Bulletin No. 43, 1987, Applied Biosystems, Foster City, Calif., illustrated in FIG. 6). Columns loaded with controlled pore glass functionalized with 5'-O-dimethoxytrityl thymidine (1 μM) were utilized. All 5'-dimethoxytrityl 3'-phosphoramidite derivatives were prepared as 0.09 M solution in anhydrous CH$_3$CN. Elongation of oligonucleotides was performed using a standard O-cyanoethyl 1 μM DNA synthesis cycle without any change in the condensation time. After automated removal of the 5'-dimethoxytrityl group, the oligonucleotides were then cleaved from the support by incubation in concentrated ammonia at room temperature for 1 hour. The deprotected oligonucleotides were purified by HPLC and for selected cases, separated into nido-[nido-7,8-C$_2$B$_9$H$_{(11\ or\ 12)}$] and closo-forms [closo-1,2-C$_2$B$_{10}$H$_{12}$] (see FIG. 6 and Table 1). Kane, R. R., Pak, R. H., Hawthorne, M. F., J. Org. Chem., 1993, 58, 991–992.

The yield for the overall synthesis of CDU-containing oligonucleotides (compounds 19–24) was comparable to unmodified (dT)$_2$ (compound 18) according to trityl release. Therefore, it appears that the presence of bulky carboranyl substituent at the 5-position of uracil does not seem to affect the efficiency of coupling reaction.

TABLE 1

| Oligomer | Structure | R$_t$ [min] | T$_m$ [° C.] [i] | T$_m$ [° C.] [j] |
|---|---|---|---|---|
| 18 | d(T)$_{12}$ | 26.4 [c] | 29.0 | 30.0 |
| 19.1 [a] | 5'CDUd(T)$_{11}$ | 18.6 [d] | 28.8 | 28.0 |
| 19.2 [a] | 5'CDUd(T)$_{11}$ | 20.0 [d] | 28.4 | |
| 19.3 [a] | 5'CDUd(T)$_{11}$ | 32.0 [d] | 28.0 | |
| 20 [b] | 5'd(T)CDUd(T)$_{10}$ | 9.4, [e] 9.9, 16.8 | 27.2 | 25.7 |
| 21.1 [a] | 5'd(T)$_6$CDUd(T)$_5$ | 12.6 [f] | 15.2 | 15.2 |
| 21.2 [a] | 5'd(T)$_6$CDUd(T)$_5$ | 13.6 [f] | 15.3 | |
| 21.3 [a] | 5'd(T)$_6$CDUd(T)$_5$ | 19.8 [f] | 15.3 | |
| 22.1 [a] | 5'd(T)$_{10}$CDUd(T) | 8.5 [g] | 20.5 | 18.5 |
| 22.2 [a] | 5'd(T)$_{10}$CDUd(T) | 9.6 [g] | 20.4 | |
| 22.3 [a] | 5'd(T)$_{10}$CDUd(T) | 20.5 [g] | 20.9 | |
| 23 [b] | 5'd(T)$_9$(CDU)$_2$d(T) | 16.6, 18.4, [h] 17.4, 17.6, 22.0–23.4, 29.0 | 15.3 | 10.0 |
| 24 [b] | 5'CDUd(T)$_9$ CDUd(T) | 18.0–19.0, [h] 22.4–23.5, 26.8, 29.1 | 20.0 | 17.0 |

[a] closo/nido oligomers were isolated by HPLC and used separately in T$_m$ experiments;
[b] closo/nido oligomers were detected by HPLC but used as mixture in T$_m$ experiments. HPLC conditions: buffer A: 0.05 M triethylammonium acetate (TEAA) (pH = 7.0), buffer B: CH$_3$CN/H$_2$O (50/50) containing 0.05 M TEAA;
[c] 25 min from 21% B to 23% B;
[d] 25 min from 26% B to 40% B, 5 min to 60% B and 5 min with 60% B;
[e] 20 min from 30% B to 55% B;
[f] 25 min from 26% B to 40% B;
[g] 25 min from 30% B to 40% B;
[h] 25 min from 30% B to 60% B and 5 min with 60% B. Tm in PIPES buffer at 120 mM NaCl.; linear plots of T$_m$ versus log(sodium ion activity) gave slopes of 15 ± 1° C.
[i] d(A)$_{12}$ was used as complementary strand for duplex formation;
[j] polyriboadenylic acid was used as target.

EXAMPLE 4

Characterization of Dodecathymidylate Containing 5-(o-carboran-1-yl)-2'--O-deoxyuridine Experimental Procedures Phosphodiesterase I (EC 3.1.4.1) type VIII from *Crotalus durissus terrificus* venom (lot 119F0730) was purchased from Sigma (St. Louis, Mo.). Polyacrylamide was purchased from International Biotechnologies Inc. (New Haven, Conn.). Bispolyacrylamide and urea were bought from Fischer Scientific (Fair Lawn, N.J.). Thermal melting curves for the oligomers were determined on a Varian Cary 4 spectrophotometer interfaced to Dell microcomputer. LSIMS mass spectra were recorded on a Finnigan MAT 95 with Cs$^+$ gun operating at 13 keV (glycerin matrix) or with VG 70-S spectrometer. CD spectra were recorded on Jasco, J-600 spectropolarimeter interfaced to an IBM computer. Polyacrylamide gel electrophoresis was performed using a BRL apparatus (Gaithersburg, Md.).

HPLC analysis of carboranyl-modified dodecathymidylate (19–24) was performed on a Hewlett-Packard 1050 system, with a Whatman Partisphere C$_{18}$ 5 μm, 4.7×235 mm column. All analyses were performed at room temperature. Typically a gradient of CH$_3$CN from 0% to 50% in 0.05 M triethylammonium acetate buffer (TEAA) pH 7.0 was used as an eluent at a flow rate of 1.0 mL/min. Retention time (Rt) values and the conditions utilized for individual oligonucleotide are shown in the Table 1.

Polyacrylamide Gel Electrophoresis (PAGE).

Labeled or unlabeled samples of modified oligonucleotides (19–24), and dodeca(thymidine phosphate) (18), prepared as described above, were separated by electrophoresis using a 20% polyacrylamide denaturing gel containing 7 M urea, for 45 min at 50 mA. The samples were visualized using standard autoradiography on X-Omat AR film (Eastman Kodak, Rochester, N.Y.) or in the case of unlabeled oligonucleotides by means of UV shadowing.

Radiolabeling of dodeca (thymidine phosphates) containing CDU (19–24). Modified oligonucleotides 19–24 and unmodified dodeca (thymidine phosphate) (18) (20 pmole of each) were incubated at 37° C. in the presence of 0.5 µL of T4 polynucleotide kinase and 10 µCi [$^{32}$P-γ) ATP (5000 Ci/mmole) in a 70 mM Tris-HCl buffer (pH 7.6) containing 10 mM $MgCl_2$ and 5 mM dithiothreitol.

The final volume of reaction mixture was 10 µL. After 30 minutes, reaction mixtures were incubated at 92° C. for 2 minutes to heat inactivate the enzyme. Thereafter, 10× tracking dye (0.5% bromophenol blue, 0.5% xylene cyanol FF, 30% glycerol in water (5 µl) was added to the reaction mixture and 5 µl aliquots analyzed by PAGE.

Melting Temperature (Tm) Measurements. Samples for $T_m$ measurements were prepared by the addition of concentrated stock solutions of the $d(T)_{12}$ (18) or CDU modified $d(T)_{12}$ (19–24) and $d(A)_{12}$ stock solution to 1.0 mL 10 mM 1,4-piperazine-bis-(ethane-sulfonic acid) (PIPES) buffer (pH 7.0) containing 100 mM NaCl, and 1 mM EDTA, in amounts to give a 1:1 ratio. Each strand was present at 40 µM. Molar extinction coefficients $\epsilon_{260}$ (per base) were calculated as following: 18: 8,150; $d(A)_{12}$: 12,280; 19–24: 8,200. The samples were heated to 85° C. and cooled slowly to room temperature before melting. The insulated cell compartment of the UV spectrophotometer was continuously warmed from 0° C. to 85° C. at the rate 0.5° C. per minute. Samples were heated in quartz cuvettes fitted with a teflon stopper (1 cm path length). The absorption change at 260 nm was followed as a function of temperature, and $T_m$ values were obtained from first derivative plots after the data were transferred to a Macintosh computer for visualization and analysis.

Circular Dichroism (CD) Measurements.

CD spectra were obtained at 10° C. in a jacketed cell flushed with nitrogen gas to prevent condensation. Samples were prepared by the addition of concentrated stock solution of oligomers 19–24 to 2.7 mL of 3.75 mM phosphate buffer (pH 7.0) containing 0.5 mM EDTA and 100 mM NaCl. To cuvettes containing the natural or modified $d(T)_{12}$ 19–24 was added $d(A)_{12}$ solution in an appropriate amount to provide a 1:1 ratio. For duplex formation, the samples were heated to 85° C. and cooled slowly to room temperature. CD spectra were obtained from 320 to 200 nm for single strands and duplexes.

Molecular Modeling.

Molecular mechanics methods with the AMBER all-atom force field and equations were used to evaluate comparative effects of the carborane cage on the stability of DNA modified at different sequence positions. The carborane was treated as a fixed structural aggregate. The effect of the carboranyl-containing base unit on local DNA conformation was evaluated.

Resistance of dodeca (thymidine phosphates) containing CDU (19–24) against phosphodiesterase I (EC 3.1.4.1): To 100 mM Tris-HCl buffer, pH 8.9 (90 µL) containing 20 mM $MgCl_2$, 0.1 $A_{260}$ ODU of oligonucleotide 19–24 (5 µL), 1.5×10-3 unit (5 µL) of phosphodiesterase was added. A blank with no enzyme, and a control reaction with $d(T)_{12}$ were assayed simultaneously. Reactions were maintained at 37° C. for 10 minutes and then 50 µL aliquots were analyzed by HPLC under conditions described above.

Results.

A difficulty in carboranyl modified oligonucleotide synthesis is the relatively easy transformation of neutral closo-form of boron cage into its nido-counterpart bearing one negative charge under basic conditions, which makes it arduous to synthesize pure closo-compounds in some cases. Using a calorimetric assay (TLC spray for detection of nido- and closo-carboranyl compounds: 30 mg $PdCl_2$ in 0.5 L of 1% HCl) and HPLC analysis, it was determined that the CDU sample used was contaminated with up to about 5% of nido-compound. The formation of the nido-isomer may occur during the deblocking of benzoylated hydroxyl functions of CDU under basic conditions. CDU modified oligonucleotides bearing boron clusters in the nido-form are characterized by lower retention time on reverse phase HPLC column (Table 1). This allows easy separation of the two components. The melting temperature measurements of the separated nido- and closo-CDU oligonucleotides indicated no significant differences in Tm for both forms of CDU modification (Table 1).

5'-End ($^{32}$P]-labeled oligonucleotides 18–24 were homogeneous as analyzed by polyacrylamide gel electrophoresis (PAGE) which demonstrated the same electrophoretic mobility. Closo-carborane derivatives can be converted easily to pure nido-form upon treatment with pyrrolidine. Kane, R. R., Lee, C.S., Drechsel, K., Hawthorne, M. F., J. Org. Chem., 1993, 58, 3227–3228. This process was used to transform CDU and $CDU(dT)_{11}$ into pure nido structure.

Figure 7:
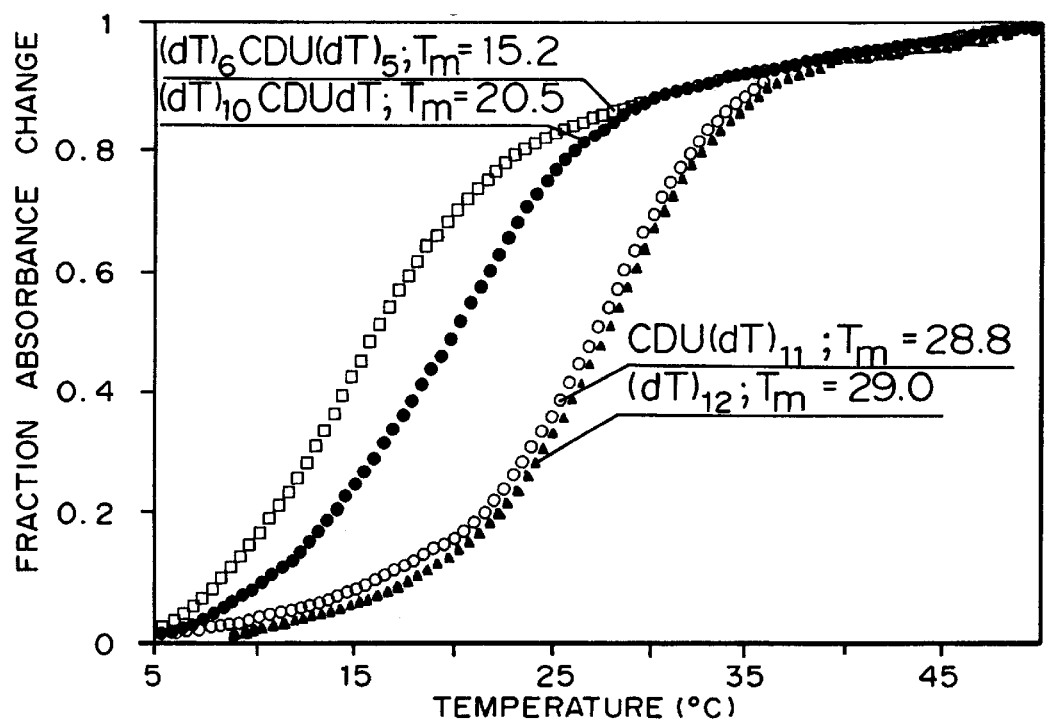
FIG. 7 is graph of the fraction of change in absorbance versus temperature in degrees Celsius for $(dT)_6CDU(dT)_5$ ($T_m$=15.2), $(dT)_{10}CDU(dT)$ ($T_m$=20.5), $CDU(dT)_{11}$ ($T_m$=28.8), and $(dT)_{12}$ ($T_m$=29.0).

Melting temperatures of the duplexes formed between CDU-modified dodecathymidylic acids and $d(A)_{12}$ strongly depended on the location of CDU in the oligonucleotide chain, and were uninfluenced by the closo/nido status of the carboranyl residue (FIG. 7 and Table 1). Thus, CDU oligonucleotides modified with CDU at the 1st (19), 7th (21) and 11th (22) position were separated into closo- and nido-derivatives by HPLC and their melting temperatures were measured independently. It was discovered that the $T_m$ for closo- and nido-form were almost identical within the same type of oligonucleotide modification (3'-, 5'-end or middle position). However, the effect of the CDU location was striking. 5'-Modifications, as well at 1st (19) as 2nd (20) position did not influence markedly the stability of the duplex compared to unmodified $(dT)_{12}$ (18); their respective $T_m$ were 28.0, 27.2 and 29.0° C. In contrast, modification in the central position of the oligonucleotide chain (position 7th, 21) caused a marked decrease of duplex stability as noted by the lowest Tm value of 15.2° C. A less pronounced effect was generated by the presence of CDU at the 11th position. The $T_m$ of the duplex formed by 3'-end modified oligonucleotide 10 decreased to 20.5° C. Inserting a second CDU nucleoside at the 3'-end (23) caused further destabilization of the duplex and decreasing the $T_m$ value to 15.3° C. Diverse consequence of 3'- and 5'-end modification upon the duplex stability was evident from above data. It seems that insertion of the CDU nucleoside at the 3'-end has a much more unfavorable effect that at the 5'-end. This is well illustrated by comparing $T_m$ values between oligonucleotides 20 and 22, where the CDU nucleotide is located respectively at the second position from the 5'-end and from the 3'-end. The difference in $T_m$ is 7–8° C. which was significant and revealed the importance of the carboranyl cluster interaction with adjacent bases.

Figure 8:
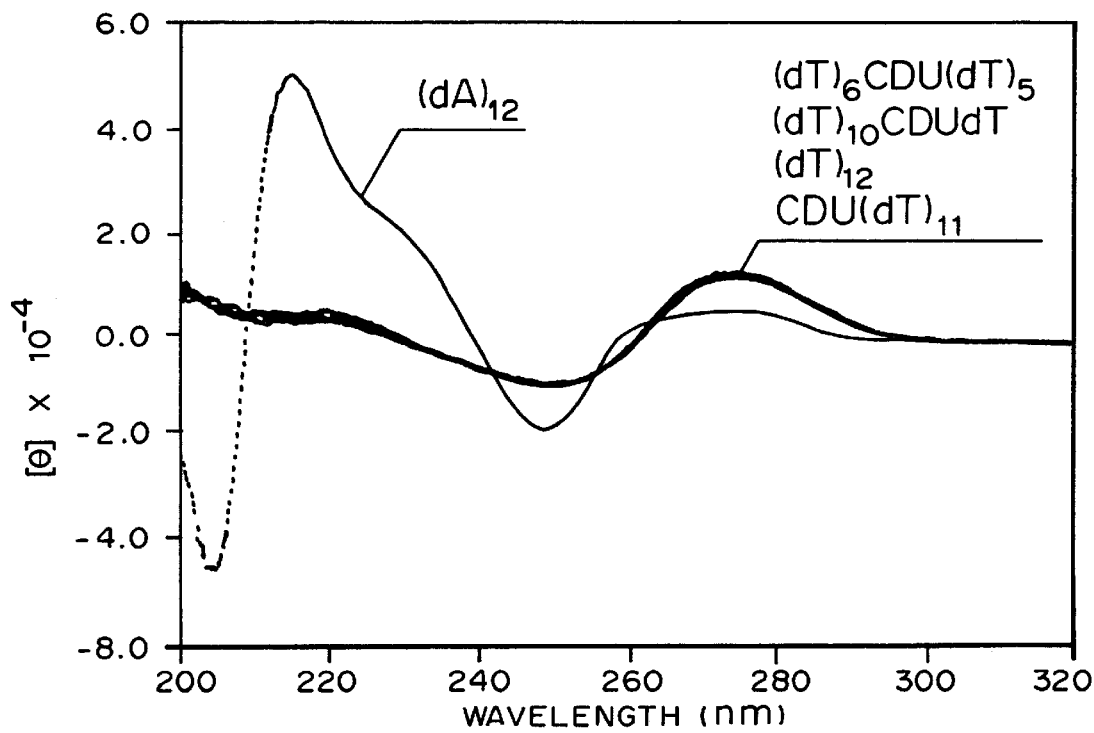
FIG. 8 is the circular dichroism spectra of selected single stranded CDU modified and unmodified $d(T)_{12}$ (compound 18).
Figure 9:
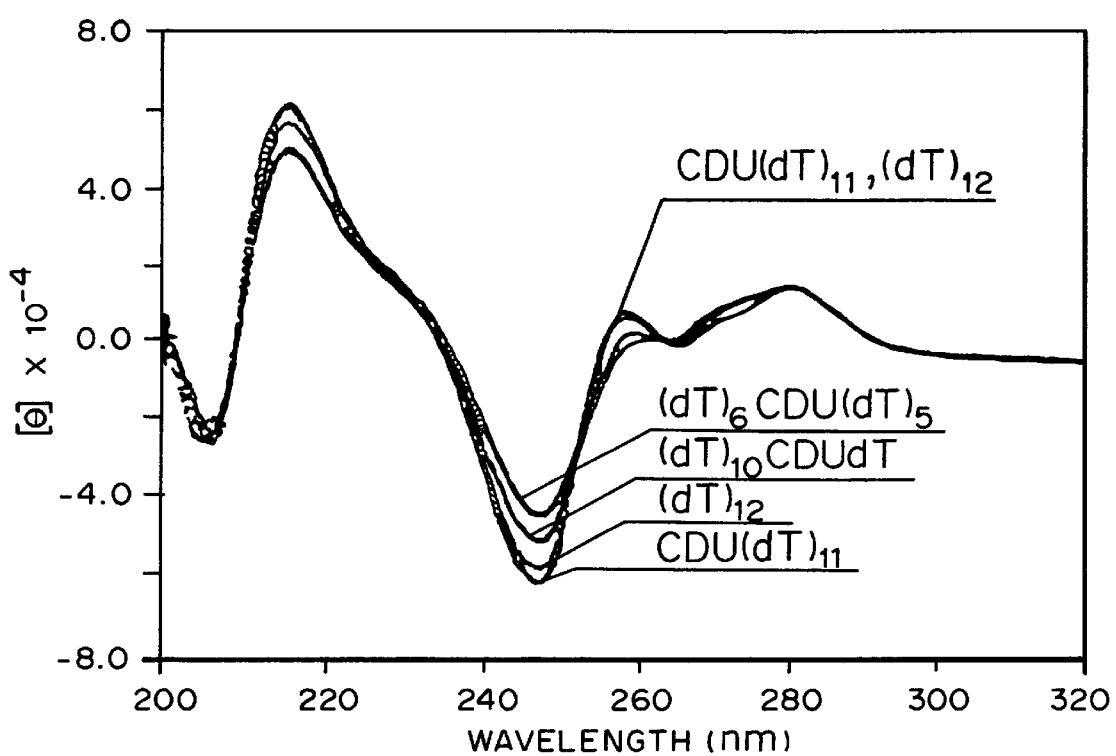
FIG. 9 is the circular dichroism spectra of complexes formed between CDU modified and unmodified $d(T)_{12}$ and $d(A)_{12}$.

These results were in agreement with $T_m$ measurements of duplexes formed between CDU modified oligomers and poly(rA). The location of CDU nucleoside within the oligonucleotide chain induced a greater destabilizing outcome which seemed more pronounced when the modification was closer to the 3'-end. Circular dichroism (CD) spectra of single stranded $(dT)_{12}$ (18) and CDU modified $(dT)_{12}$ (19–24) recorded under analogous conditions were almost identical in term of their shapes and molecular ellipticity value (see FIG. 8). This suggests identical conformation in solution for the carboranyl oligomers compared to $(dT)_{12}$ (18) standard. The CD spectra of duplexes formed between CDU modified oligothymidylates (20–24) and unmodified $(dT)_{12}$ (18) and $(dA)_{12}$ showed a reduction in the magnitude of molecular ellipticity at 246 nm which correlated with increased thermal stability of the duplexes (FIG. 9).

The stability of the oligonucleotides against nucleases is an important factor for in vivo applications. It is known that 3'-exonuclease activity is responsible for most of the unmodified antisense oligonucleotide degradation in serum. Vlassov, V. V., Yakubov, L. A., in Prospects for Antisense Nucleic Acid Therapy of Cancers and AIDS, 1991, 243–266, Wiley-Liss, Inc., New York; Nucleic Acids Res., 1993, 21, 145.

The replacement of all natural phosphodiester linkages within oligonucleotide chain by methylphosphonate ones is an example of modifications that ensure complete stability of the oligonucleotide towards exo- and endonucleases. To test the resistance of CDU-oligonucleotides towards 3'-exonucleolytic activity (hydrolysis of the oligonucleotide from 3'-end), snake venom phosphodiesterase (SVPD) from *Crotalus durissus terrificus* was used. It was discovered that these oligonucleotides are remarkably stable to 3'-exonucleases if the CDU residue is incorporated in the 3'- or both 3'- and 5'-end. The oligonucleotide bearing both 3'- and 5'-modifications (24) was also resistant to SVPD and calf spleen phosphodiesterase.

Modified oligonucleotides with carboranyl-containing bases may also serve as primers for various polymerases including human immunodeficiency reverse transcriptase.

To evaluate comparative effects of the carborane cage on the stability of double stranded DNA modified at different position, molecular mechanics methods were applied. For this purpose, the AMBER all-atom force field method (Singh, U. C., Weiner, P. K., Caldwell, J., Lollman, P. A. AMBER 3.0, University of California: San Francisco, Calif., 1986). There were significant unfavorable interactions of the carborane substituent with adjacent bases, and the interactions were asymmetric in orientation due to the right-handed twist of DNA (see FIG. 10). This is in agreement with observed striking differences of duplex thermal stability between 5'- and 3'-CDU modified $(dT)_{12}$ (19–24). For example, the oligonucleotide 5'-CDUd$(T)_{11}$ (19.1) is characterized by a $T_m$ Of 28.0° C. compared to a $T_m$ of 15.2° C. for 5'd$(T)_6$CDUd$(T)_5$ (21.1) (Table 1). Energy minimization results with $(dT)_{12}$·$(dA)_{12}$ showed that substitution on the 5'end of the $(dT)_{12}$ strand gave overall helix energies that were significantly lower than for duplex substituted on the 3' side of $(dT)_{12}$. Substitution on the interior bases of the duplexes caused even larger helix destabilization.

With the 5' substituted duplex there is little interaction of the carborane with bases and the overall helix geometry is similar to the unsubstituted duplex. At the 3' end of the duplex the bases can distort to relieve some of the strain from the steric clash due to end effects and freedom of motion of base pairs at the end of the double helix. CDU substituted bases in the center of the helix have similar steric clash, but they do not have the flexibility of base pairs at the 3' end of the helix.

EXAMPLE 5

Kinetic Study of CDU-Oligonucleotides Stability Towards SVPD 3'-exonuclease

The half-life (T½) of 3'-CDU-, 3',5'-CDU- and 3'CDU$_2$- oligonucleotides were determined by kinetic study of their degradation by SVPDE (snake venom phosphodiesterase). Aliquots of enzymatic reaction (0, 5, 10, 20, 40, 80 and 240 minutes) were analyzed by HPLC. Calculations of half life time were based on the disappearance of 12-mer (or 11-mer in the case of CDU-modified oligos) after standardization with 2'-deoxycytidine used as internal standard. The results are provided in Table 2.

TABLE 2

| Time (min) | % of d$(T)_{12}$ 18 remaining | % of 3'- CDU 22 remaining | % of 3',5'- CDU 24 remaining | % of 3'- CDU$_2$ 23 remaining |
|---|---|---|---|---|
| 0 | 100 | 100 | 100 | 100 |
| 5 | 9.1 | 54.8 | 56.2 | 82.0 |
| 10 | 2.6 | 44.0 | 38.1 | — |
| 20 | — | 38.3 | — | 80.0 |
| 40 | — | 23.2 | 14.8 | 78.9 |
| 80 | — | 11.0 | — | 54.0 |
| 240 | — | — | — | 10.5 |
| T½ (min) | 0.5 | 6.7 | 5.06 | 76.2 |
| ®(cor coef) | 0.998 | 0.996 | 0.998 | 0.920 |

III. Determination of other Properties of Modified oligonucleotides

Methods for the evaluation of the aqueous and serum stability, cellular uptake, cellular washout, and partition coefficient for the compounds described herein are provided below. In a preferred (but not required) embodiment, the selected compound for in vivo purposes exhibits an aqueous stability under the conditions described below of at least one hour, a serum stability of at least one hour, a cellular uptake of at least 1% of the dose, a cellular washout of at least 1 hour, and a partition coefficient indicative of suitable lipophilicity.

Oligonucleotide Stability Studies.

(a) In buffer: Five samples (pH 3–7) are prepared by dissolving 10 ODU of oligonucleotide in 100 µl of appropriate 0.2 M phosphate buffer (KHPO$_4$/KOH/H$_3$PO$_4$) and maintained at 4° C., 22° C., and 37° C. At the designated time intervals, 10 pl aliquots of each solution are analyzed by HPLC. The concentration of the mixture components is calculated as a percentage of the total area under the curve for the oligonucleotide and presumed decomposition product.

(b) Oligonucleotide stability in human, mouse, and rat serum: The stability of the oligomers is determined by incubating the nucleotides at 37° C. for the desired period and, after precipitating the protein with cold 60% MeOH/H$_2$O and lyophilizing the supernatant, the sample is resuspended in buffer and an aliquot analyzed by HPLC. A reverse-phase Merck RP-18, 5 mm×25 cm column is used to determine the stability of the oligonucleotides. The mobile phase is acetonitrile in triethylammonium acetate (or similar system). An isocratic flow of 1 mL/min is used, and the peaks are monitored using a UV detector set at 260 nm.

Cellular Uptake Studies.

Triplicate studies are undertaken using unlabeled or radiolabeled oligonucleotide in order to follow the intracellular profiles of the drug. For example, human glioma cells U251 (2×10$^6$ cells) are suspended in medium containing 10% fetal calf serum and antibiotics, and incubated at 37° C. in a 5% CO$_2$ incubator. The experiment is initiated with addition of 2–10 µM [$^3$H]-oligomer (specific activity ~1,000–2,000 DPM/pmole), and cells are exposed for 1, 2, 4, 6, 12, and 24 hours to the drug. Medium is removed and the cells are washed 3 times with cold Hank's balanced salt solution. Extraction is performed with addition of 1 mL of 60% cold methanol/water, followed by storage overnight at −70° C.

The suspensions are then centrifuged and the supernatants are lyophilized to dryness. The residues are resuspended in 250 μL of water, and aliquots containing 50–100 μL are analyzed by HPLC. Quantitation of intracellular oligomer are conducted by HPLC methods developed in our laboratory. A buffer system close to physiological pH is used if needed.

Cellular Washout Studies.

Studies are performed using unlabeled or radiolabeled agent in order to follow the intracellular profiles of the oligomer detected within the cells after removal of drug at different times after pulsing. Cells ($2 \times 10^6$ cells) are suspended in the appropriate medium supplemented with serum and incubated at 37° C. in a 5% $CO_2$ incubator. Radiolabeled drug concentrations to be utilized are 2 and 10 μM. After pulsing the cells with the labeled compound for the desired time, the cells are thoroughly washed and then replenished with fresh medium without the drugs (O h). At 0, 2, 4, 6, 8, 24, and 48 h (second incubation times), the cells are removed and immediately extracted with 60% cold methanol/water. The extracts are obtained by centrifugation and removal of the cell pellet. The extracts are lyophilized and stored at −70° C. The material is resuspended in 200 μL of HPLC buffer and immediately analyzed. Quantitation of intracellular oligomers is conducted as described above.

Partition Coefficient Determination.

The oligonucleotide (1 mg/mL) is dissolved in water and then 1 mL octanol is added. The compound is allowed to partition between the two solvents by shaking for 2 hours. The concentration of the drug is determined in different phases by HPLC, as described above.

IV. Method of Use of Carboranyl-Containing Nucleosides and oligonucleotides

A. Use in Boron Neutron Capture Therapy

The carboranyl-containing nucleosides and oligonucleotides described herein can be used in boron neutron capture therapy to treat a variety of disorders, and in particular, cancer, for example brain gliomas, melanomas, and breast cancer. BNCT techniques are well known to those of skill in the art, and are described in detail, for example, in Hatanaka et al, *Z. Neurol.*, vol. 204, pp. 309–332 (1973); Tolpin et al, *Oncology*, vol. 32, pp. 223–246 (1975); U.S. Pat. Nos. 5,130,302; 5,066,479, 5,021,572, 4,959,356, and 4,855,493; and Barth et al, *Cancer Res.*, vol. 50, pp. 1061–1070 (1990). As an example, a patient in need thereof is treated with an effective amount of one or more to the disclosed compounds and then exposed to neutrons, preferably epithermal neutrons which should not exceed $5 \times 10^{12}$ n/cm$^2$ (total dose). A preferred dose of carboranyl-containing nucleoside or oligonucleotide, or combination thereof, for this purpose is 0.01 to 100 mg/kg of body weight in single dose and preferably 0.1 to 20 mg/kg of body weight in a single dose administered intravenously. It may be advantageous to pulse the dosage in order to accumulate the compound in certain cells, such as glioma cells. The compound can be administered at any suitable time, and is typically administered thirty minutes to one hour prior to neutron irradiation.

B. Anti-Viral Activity

A number of the carboranyl-containing compounds disclosed herein exhibit antiviral activity, including anti-HIV or anti-HBV activity. The compounds can be easily evaluated for anti-HIV activity using a variety of methods, for example those disclosed in European Patent Application Nos. 92304551.2 and 92304552.0 filed by Biochem Pharma, Inc.; PCT Publication Nos. WO 92/14729 and WO 92/14743 filed by Emory University, and Schinazi, et al., *Antimicrobial Agents Chemother.*, 34, page 1061 (1990.).

The ability of the boron cluster nucleosides to inhibit HBV can also be measured by various experimental techniques. A common assay used to evaluate the ability of the disclosed compounds to inhibit the replication of HBV is described in detail in Korba and Gerin, *Antiviral Res.* 19: 55–70 (1992).

C. Ability of Boron Cluster Oligonucleotides to Effect Site-Directed Mutagenesis Site Directed Mutagenesis (SDM) is a known technique in which mutations are effected in nucleic acid sequences that encode proteins. In general, a synthetic oligonucleotide is initially hybridized to a target nucleic acid sequence in vivo or in vitro under standard conditions. (Baumgart, P. M., Kliem, H -C., Gottfried-Anacker, J., Wiessler, M., Schmeiser, H. H., 1993, Nucl. Acids Res., 21, 3755–3760). On transcription or translation of the nucleic acid sequence, a defective nucleic acid or amino acid sequence, respectively, is produced.

It has been discovered that the synthetic boron cluster-containing oligonucleotides disclosed herein can be used to effect site directed mutagenesis in vivo or in vitro. In particular, a viral, eukaryotic or prokaryotic genome can be mutated by inserting a carboranyl-containing oligonucleotide into a cell wherein the oligonucleotide hybridizes to a nucleic acid sequence in a manner that causes a mutation during transcription or cell division. Examples of viral nucleic acids that can be mutated include those in HIV and hepatitis viruses, including HBV.

As one example, mutagenic oligonucleotides and mutant *E. coli* strains lacking a DNA repair mechanism (or nested PCR) can be used to effect mutations of expressed HIV-1 reverse transcriptase. Because mutant repair minus DNA polymerases and RT function similarly, it is possible to perform site directed mutagenesis in vivo during HIV-1 RNA reverse transcription in order to effect subsequent expression of integrated viral genome. Expression of the mutated RT gene at the further stages of virus replication cycle results in production of unfunctional enzyme which in turn can inhibit viral replication. Mutations in other target areas of HIV can also be generated as desired using the appropriate sequence.

Example 6 describes the in vivo mutation of the RT gene within the YMDD motif, incorporated into a proper vector in *E. coli* cells. The mutagenic oligonucleotide DNA target region is the conserved YMDD motif (nucleotides 5' 2678 to 3' 2689) of HIV-1 RT. The mutagenic oligonucleotides used were 5'-AATACATGGA(CDU)GATTTGTAT-3' (SEQ ID NO:1) and 5'-AATACATGG(CDU)(CDU)GATTTGTAT-3' (SEQ ID NO:2). The oligonucleotides were synthesized using β-cyanoethyl phosphoramidite chemistry and an automated DNA synthesizer. Each contains one or two modified nucleosides [(5-(o-carboran-1-yl)-2'-deoxyuridine (CDU)].

EXAMPLE 6

Site-Directed Mutagenesis of RIV-1 Reverse Transcriptase

HIV Cloning

A restriction map of the molecular infectious clone, pBRU, was generated using a system 7 DNASTAR program (DNASTAR Inc., Madison, Wis.). The restriction enzymes used for the cloning of the reverse transcriptase (RT) gene were selected to contain the active site of RT and to ensure unique restriction sites for the cloning of mutants back into PBRU. The restriction enzymes Sac 1 (base 228) and Sal 1 (base 5367) were used to place the desired fragment into the phagemid pALTER-1. This plasmid was supplied with the Altered Sites in vitro Mutagenesis System (Promega Corp., Madison, Wis. 53711-5399). Positive clones for the RT insertion into pALTER-1 were selected by sequencing from the T7 primer site (5'-AACAGCTATGACCATG-3') (SEQ ID NO: 19) (GIBCO BRL., Gaithersburg, Md.). Sequencing was performed using a Sequenase version 2.0 kit (United States Biochemical Corp., Cleveland, Ohio.). The construct was transformed into JM109 (endA1, recAl, gyrA96, thi, hsdR17 (rk⁻, $m_k^+$), relA1, supE44, lambda⁻, Δ(lac-proAB), [F', traD36, proA⁺B⁺, lacI$^q$ZΔM15] using the method of CaCl$_2$ transformation as described (Sambrook, J., Fritsch, E. F., Maniatis, T., 1989, Molecular Cloning. A Laboratory Manual, (Nolan, C., Ed.) Cold Spring Harbor Laboratory Press).

Preparation of Single Stranded DNA overnight cultures of the JM109 (pHIVALT-1) construct were grown in 2 mL of TYP broth (16 g Bactone-tryptone-16 g Bacto-yeast extract-5 g NaCl/liter) containing 15 μg/mL tetracycline (tet) shaking 200 rpm at 37° C. The following morning 5 mls of TYP broth containing 15 μg/mL tet plus 2.5 g/L K$_2$HPO$_4$ was inoculated with 100 μL of overnight culture. The culture was shaken vigorously at 37° C. for 30 min in a 50 mL flask. The culture was then infected with R408 and M13K07, helper phages, at a multiplicity of infection (m.o.i.) of 10. The cultures were then shaken at 200 rpm overnight at 37° C. The next morning the culture was harvested by spinning at 12,000 rpm for 15 minutes, and the supernatant was removed to a new tube. The supernatant was then spun again at 12,000 rpm for 15 min to remove any remaining cells or debri. The phage was then precipitated by adding 0.25 volumes of a polyethylene glycol (PEG) solution (3.75 M ammonium acetate-20% polyethylene glycol; MW 8,000). The sample was then placed on ice for 30 min, followed by centrifugation at 12,000× g for 15 min. The pellet was thoroughly drained by inverting the tube on a paper towel for 2–3 min. The pellet containing phage was then resuspended using 400 μL of TE buffer (10 mM Tris-HCl (pH 8.0, 1 mM EDTA)]. An equal volume of chloroform:isoamyl alcohol (24:1) was added directly to the resuspended phage in order to lyse the particle and to remove any excess PEG solution. The mixture was inverted several times and spun at 12,000× g for 5 min. The upper aqueous phase was removed to a new tube and an equal volume of TE saturated phenol:chloroform:isoamyl alcohol (25:24:1) was added. The solution was then inverted several times and spun at 12,000× g for 5 min. This step was repeated until no visible interface could be detected. From the final phenol:chloroform:isoamyl alcohol extraction, the aqueous phase was removed to a new clean eppendorf tube. Finally, 0.5 volumes of 7.5 M ammonium acetate and 2 volumes of ice cold 95% EtOH was added to the solution. The solution was placed at −70° C. undisturbed. After 1 hour, the sample was spun at 14,000× g for 30 minutes followed by two washes with 70% EtOH at 14,000× g for 15 minutes each. The sample was then dried in a speed vac at room temperature for 10 min. Samples were then resuspended in 20 μL of dH$_2$O and spot checked on ethidium stained 0.8% agarose gel run at 45 volts for approximately 1.5 hour.

Oligonucleotide Preparation

Automated synthesis of 5'-AATACATGGA(CDU) GATTTGTAT-3' (SEQ ID NO:1) and 5'-AATACATGG (CDU)(CDU)GATTTGTAT-3' (SEQ ID NO:2). The modified oligonucleotides were synthesized using an Applied Biosystems 391 DNA synthesizer. Columns loaded with controlled pore glass functionalized with 5'-O-dimethoxytrityl thymidine (1 mM) were utilized as solid support. All 5'-dimethoxytrityl 3'-phosphoramidite derivatives were prepared as 0.09 M solution in anhydrous CH$_3$CN. Elongation of oligonucleotides was performed using standard β-cyanoethyl 1 mM DNA synthesis cycle (*Applied Biosystems USER Bulletin No.* 43, 1987, Applied Biosystems, Foster City, Calif.) without any change in the condensation time. Oligonucleotides were then deprotected and cleaved from the support by overnight incubation in concentrated NH$_4$OH at room temperature. The oligonucleotides were then purified using OPC™ cartridge (Applied Biosystems, Foster City, Calif.) and their purity was checked by HPLC as described below.

HPLC analysis of 5'-AATACATGGA(CDU)GATTTGTAT-3' (SEQ ID NO:1) and 5'-AATACATGG(CDU)(CDU) GATTTGTAT-3' (SEQ ID NO:2). HPLC analysis was performed using Hewlett-Packard 1050 system, using Whatman Partisphere C$_{18}$ 5 μm, 4.7×235 mm column. All analyses were performed at room temperature. Typically, a gradient of CH$_3$CN from 5% to 30% in 0.05 M triethylammonium acetate buffer (TEAA) pH 7.0 was used as eluent at a flow rate of 1.0 mL/min. 5'-AATACATGGA(CDU) GATTTGTAT-3, $R_t$ 14.83 min; AATACATGG(CDU)(CDU) GATTTGTAT-3', Rt 14.64 min.

In vitro Site Directed Mutagenesis

The procedure for in vitro site directed mutagenesis used in this experiment was a modification of that used in the Altered Sites mutagenesis Kit #Q6210 (Promega Corp., Madison, Wis.). Briefly, oligonucleotides, 5'-AATACATGGA(CDU)GATTTGTAT-3' (SEQ ID NO:1) and 5'-AATACATGG(CDU)(CDU)GATTTGTAT-3' (SEQ ID NO:2), and a control, located on the putative catalytic active site for HIV-1 RT (5'-2676 to 3'-2696) were 5' phosphorylated using T4 polynucleotide kinase. The reaction was terminated by heating to 70° C. for 10 min. The mutagenesis annealing reaction was performed by adding 0.05 pmol of pHIVALT-1 ssDNA, 0.25 pmol ampicillin repair oligonucleotide (supplied in the kit), 1.25 pmol of the 5' phosphorylated mutagenic oligo, and an annealing buffer supplied in the kit in a final volume of 20 μL. The control oligonucleotide reactions for this experiment were done separately along with an added reaction that contained ampicillin repair oligo but no mutagenic oligo 5'-AATACATGGA(CDU)GATTTGTAT-3' (SEQ ID NO: 1) and 5'-AATACATGG(CDU)(CDU) GATTTGTAT-3' (SEQ ID NO:2) and control unmodified. The reactions were then heated to 70° C. for 5 min and allowed to cool to room temperature over a 15–20 min period. The annealing reactions were placed on ice and the following reagents were added: 3 μL 10× synthesis buffer (supplied in kit), 1 μL T4 DNA polymerase (10 U/μL), 1 μL T4 DNA ligase (2 U/μL), and 5 μL sterile dHO. The 30 μL reaction was incubated at 37° C. for 90 min to perform second strand synthesis and ligation.

Mutagenesis

In order to observe the effects of the CDU modified oligonucleotides on mutagenesis, the entire reaction mixture (30 μL) from the in vitro mutagenesis step (above) was added to competent BMH 71-18 mut S (thi, supE, Δ(lac-proAB), [mutS:Tn10] [F', proA⁺ B⁺, laqI$^q$ZΔM15] a repair minus strain and DH5δ a repair positive strain. The reaction mixture was then transformed by CaCl$_2$as described by Maniatis et al. One portion of the transformants were plated on Lennox L agar (LB agar) (Gibco-BRL, Madison, Wis. cat # M27000B) plus 100 μg/mL ampicillin and the other was placed in 5 mL LB broth containing 100 μg/mL ampicillin for mutant selection from the BMH 71-18 mut S transformants only.

Mutant Selection for Sequencing

Transformed BMH 71-18 mut S from control and experimental reactions were grown overnight in 5 mL LB broth containing ampicillin 100 µg/mL shaken 250 rpm at 37° C. Overnight cultures were spun down and lysed for plasmid extraction using the Qiagen Plasmid Kit # 12123 tip-20 (Qiagen Inc., Chatsworth, Calif. 91311). Procedures for plasmid extraction were followed according to manufacterers specifications with no special modifications. The following morning the entire culture was centrifuged and lysed as described above. After retrieval of the plasmid DNA from BMH 71-18 mut S, the purified plasmid DNA was resuspended in 20 µL of sterile $dH_2O$ and transformed into competent JM109 as described above and plated on LB agar plates supplemented with 100 µg/mL ampicillin.

Sequencing

Sequencing was performed by the cycle sequencing method from an AmpliTaq Sequencing Kit (Perkin Elmer Cetus Corp., Norwalk, Conn.). The primers used for the sequencing of mutants were RT-MT4 (5'-CAATGAGACACCAGGG-3') (SEQ ID NO:20) located 5'-2539 to 3'-2554 of HIVBRU, and RT-MT7RC (5'-GTCATTGACAGTCCAGCTGTC-3') (SEQ ID NO:21) located on the opposite strand 5'-2899 to 3' 2879. The primers are located on opposite sides of the active site of RT and would give sequence verification on both strands of the plasmid.

Results

Mutagenesis

The in vitro mutagenesis reactions containing CDU modified oligomers [5 '-AATACATGGA(CDU)GATTTGTAT-3' (SEQ ID NO:1) and 5'-AATACATGG(CDU) (CDU)GATTTGTAT-3'] (SEQ ID NO:2) and the control reactions were placed in repair positive and repair minus strains of E. coli. The reactions containing ampicillin (amp) repair oligo plus natural oligo (excluding CDU modification) in a repair positive strain (DH5δ) of E. coli, failed to produce colonies on the amp plates but did, however, produce colonies on tetracycline (tet) plates. The control reactions transformed into the repair minus strain (BMH 71-18 mut S) produced colonies on ampicillin and tet plates. Reaction mixtures from the experimental mutagenic CDU modified transformations into the repair positive strain demonstrated a lack of ability to form colonies on amp or tet plates. However, the reactions from the CDU modified in vitro mutagenesis in the repair minus strain demonstrated the ability to grow on amp plates and finally after transformation into JM109, demonstrated amp and tet resistance.

Sequencing

Sequencing of the mutants formed from in vitro site directed mutagenesis using 5'-AATACATGGA(CDU) GATTTGTAT-3' (SEQ ID NO:1)(RL-1) and 5'-AATACATGG(CDU)(CDU)GATTTGTAT-3' (SEQ ID NO:2) (RL-2), and control oligonucleotides was carried out. In 60% of the clones (using RL-1), the mutation occurred next to the base opposite to CDU on the complimentary strand (e.g., 5'-AATACATGGTTGATTTGTAT) (SEQ ID NO:22), leading to an amino acid change from YMDD to YMVD. A sequence change of YMDD to YMGD was also observed in this case.

The second sequence (RL-2) caused an amino acids change from YMDD to YRVD in the percentage of the clones.

D. Use of Oligonucleotides as Probes

The oligonucleotides of the present invention can be used as probes in a variety of diagnostic techniques, including Magnetic Resonance Imaging (MRI). MRI is a noninvasive technique used to detect the presence and location of tumors in a patient. For example, cancer cell specific boronated compounds are administered to a patient which concentrate in the cancerous tissue. The MRI instrument is capable of detecting and locating regions of abnormal concentrations of boron. By indicating the regions having high relative concentrations of boron, MRI establishes the presence and location of the tumors.

Another diagnostic application of the oligonucleotides of the present invention is their use as molecular probes. The oligonucleotide is used to detect the presence of complementary sequences of DNA or RNA in a sample by hybridization according to standard techniques. For example, the probes can be used in a Southern blotting and Northern blotting assay, the details of which are known. See, e.g., R. Old and S. Primrose, Principles of Gene Manipulation, 8–10 (3d Ed. 1985). When used as probes, the boron atom serves as a radiolabel, though it is not itself radioactive until exposed to neutron radiation. When exposed to neutrons, $^{10}B$ absorbs a neutron and forms unstable $^{11}B$, which rapidly decays and releases an alpha particle and gamma radiation, thus providing a detectable signal. The techniques involved in the generation of the alpha particle are known. See, e.g., A. Soloway, Borax Rev. 3, 7–9 (1988).

Reaction conditions for hybridization of an oligonucleotide probe or primer to a nucleic acid sequence vary from oligonucleotide to oligonucleotide, depending on factors such as oligonucleotide length, the number of G and C nucleotides, and the composition of the buffer utilized in the hybridization reaction. Moderately stringent hybridization conditions are generally understood by those skilled in the art as conditions approximately 25° C. below the melting temperature of a perfectly base-paired double-stranded DNA. Higher specificity is generally achieved by employing incubation conditions having higher temperatures, in other words more stringent conditions. Chapter 11 of the well-known laboratory manual of Sambrook et al., MOLECULAR CLONING: A LABORATORY MANUAL, second edition, Cold Spring Harbor Laboratory Press, New York (1990) (which is incorporated by reference herein), describes hybridization conditions for oligonucleotide probes and primers in great detail, including a description of the factors involved and the level of stringency necessary to guarantee hybridization with specificity.

E. Detection of Boron in Tissue Samples

The technique developed by Ganbel, et al. (Gabel, D., Hocke, I., and Elsen, W., Determination of sub-ppm amounts of boron-10 solutions by means of solid state track detectors. Phys. Med. Biol. 28:1453–1457, 1983; Fairchild, R. G., Gabel, D., Laster, B., And Kiszenick, W. B-10 Analysis in Tissue by Prompt-gamma and Track Etching Techniques. Proc. the First International Symposium on Neutron Capture Therapy, Oct. 12–14, 1983. BNL Report No. 51730, pp. 106–13, 1984) is used, in which cellulose nitrate film is used to detect ng amounts of natural boron in 0.5 mg. droplets (1.2). Small (0.5 µl) droplets containing known or unknown amounts of boron are deposited on cellulose nitrate film (kodak Pathe type LR115), dried, and then irradiated with=$6 \times 10^{12}$ $n/cm^2$. The resulting alpha tracks are etched with NaOH, and then counted optoelectronically. The boron content in $10^6$ cells ($\cong$1 mg of tissue or sample) can be obtained by lysing the cells to be analyzed, and then proceeding as described above. This procedure can be easily adapted by one of skill in the art for diagnosis using the boron containing probes.

F. Antisense Therapy

Oligonucleotides of the present invention which are capable of binding to polyribonucleic acid or polydeoxyribonucleic acid are useful as antisense agents in the same manner as conventional antisense agents. See generally Antisense Molecular Biology and S-oligos, *Synthesis* 1 (October 1988) (published by Synthecell Corp., Rockville, Md.); 2 Discoveries in Antisense Nucleic Acids (C. Brakel and R. Fraley eds. 1989); Uhlmann, et. al., "Antisense Oligonucleotides: A New Therapeutic Technique," *Chem. Rev.* 90(4), 1990; and Milligan, J. F., Matteucci, M. D., Martin, J. C., J. Med. Chem., 1993, 36, 1923–1937. Antisense agents of the present invention may be used by constructing an antisense agent which is capable of selectively binding to a predetermined polydeoxyribonucleic acid sequence or polyribonucleic acid sequence to a cell containing such sequence (e.g., by adding the antisense agent to a culture medium containing the cell) so that the antisense agent is taken into the cell, binds to the predetermined sequence, and blocks transcription, translation, or replication thereof. The requirements for selective binding of the antisense agent are known (e.g., a length of 17 bases for selective binding within the human genome).

V. Pharmaceutical Compositions and Delivery of Carboranyl-Containing Nucleosides and Oligonucleotides The carboranyl-modified nucleosides and oligonucleotides and any combinmation thereof, can be administered to humans in an effective amount for any of the purposes described herein. The active material can be optionally be administered as a pharmaceutically acceptable derivative or salt, or optionally, in combination with a pharmaceutically acceptable carrier or diluent. The active materials can be administered by any appropriate route, for example, orally, parenterally, intravenously, intradermally, subcutaneously, or topically, in liquid or solid form.

The active compound is included in the pharmaceutically acceptable carrier or diluent in an amount sufficient to deliver to achieve the desired therapeutic result without causing serious toxic effects in the patient treated. For the treatment of disease such as cancer or a virus, in general, compounds with a therapeutic index of at least 2, and preferably at least 5 or 10, are acceptable. The therapeutic index is defined as the $IC_{50}/EC_{50}$, wherein $EC_{50}$ is the concentration of compound that inhibits the growth by 50% of the diseased cells and $IC_{50}$ is the concentration of compound that is toxic to 50% of the otherwise healthy target cells. Cellular toxicity can be measured by direct cell counts, trypan blue exclusion, or various metabolic activity studies such as $^3H$-thymidine incorporation, as known to those skilled in the art.

A preferred dose of the active compound for all of the above-mentioned conditions will be in the range of 0.01 to 1000 mg/kg of body weight and preferably 0.1 to 20 mg/kg of body weight in a single dose per day. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The compound is conveniently administered in unit any suitable dosage form, including but not limited to one containing 5 to 3000 mg, preferably 70 to 1400 mg of active ingredient per unit dosage form. A oral dosage of 50–1000 mg is usually convenient.

Ideally the active ingredient should be administered to achieve peak plasma concentrations of the active compound of from about 0.01 to 100 $\mu$M, preferably about 0.1 to 40 $\mu$M. This may be achieved, for example, by the intravenous injection of a 0.1 to 2% solution of the active ingredient, optionally in saline, or administered as a bolus of the active ingredient.

In a preferred embodiment for BNCT, the active compound is administered in an intravenous solution with a dose ranging from 1 mg/kg to 20 mg/kg. In a preferred embodiment for antisense therapy, the active compound is administered in a pharmaceutical composition for oral delivery that protects the compound from the acid environment of the stomach, for example, an enteric coating.

The concentration of active compound in the drug composition will depend on absorption, inactivation, and excretion rates of the drug as well as other factors known to those of skill in the art. It is to be noted that, when using the compound to treat a disease, dosage values will vary depending on the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The active compound or a pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable derivative or salt thereof can also be mixed with other active materials that do not impair the desired action, or with materials that supplement the desired action, such as antibiotics, antifungals, antiinflammatories, or other antivirals, including other nucleoside anti-HIV compounds.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers. are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Scios-Nova Pharmaceuticals, Inc.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives are then introduced into the container. The container is then swirled by hand to free lipid material from the sides of the container and to disperse lipid aggregates, thereby forming the liposomal suspension.

This invention has been described with reference to its preferred embodiments. Variations and modifications of the invention will be obvious to those skilled in the art from the foregoing detailed description of the invention. It is intended that all of these variations and modifications be included within the scope of the appended claims.

We claim:

1. A method for conducting boron neutron capture therapy, comprising administering to a patient in need thereof an effective amount of an oligonucleotide that contains at least one uncharged 3',5'-O,O-[(carboran-1-yl-methyl)phosphonate] internucleotide linkage.

2. A method for conducting boron neutron capture therapy, comprising administering to a patient in need thereof an effective amount of an oligonucleotide that contains at least one carboranyl-containing base of the formula:

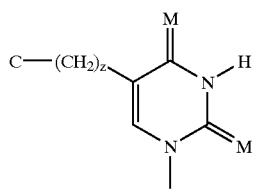
V.

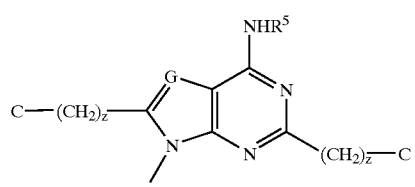
VI.

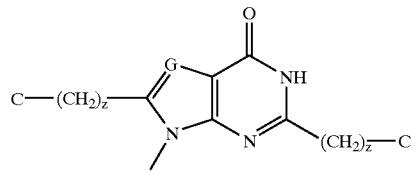
VII.

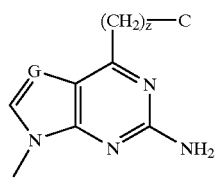
VIII.

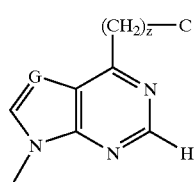
IX.

-continued

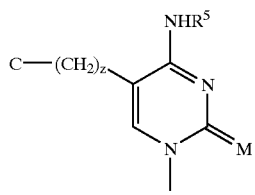

X.

wherein:
C is a carboranyl group such as $B_{10}H_{10}C_2R_4$, wherein $R_4$ is —H, —OH, —CH$_2$OH, —CH$_2$X (wherein X is halogen) or —$B_9C_2H_{(11\ or\ 12)}$ (a nido-carborane anion);
$R^5$ is lower alkyl;
G is N or CH;
M is O or S; and
z is 0 to 5.

3. A method for conducting boron neutron capture therapy, comprising administering to a patient in need thereof an effective amount of a compound selected from the group consisting of the following:

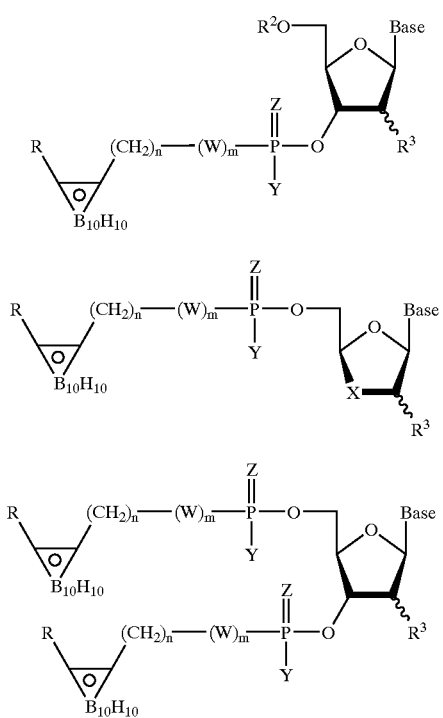

wherein:
$R^1$ is alkyl, haloalkyl, alkenyl, alkoxyalkyl, aryl, heteroaryl, trifluoromethyl, alkylaryl, arylalkyl, or halogen;
$R^2$ is hydrogen, alkyl, acyl (including acetyl); sulfonate ester including alkyl or arylalkyl sulfonyl including methanesulfonyl; a mono-, di- or triphosphate ester; trityl or monomethoxytrityl; benzyl, wherein the phenyl group is optionally substituted with one or more substituents as described in the definition of aryl given above; silyl, including trialkylsilyl (e.g. dimethyl-t-butylsilyl) or diphenylmethylsilyl; lipid; peptide; or cholesterol;
$R^3$ is hydroxyl, hydrogen, halogen, —CN, —N$_3$, lower alkyl, amino, alkylamino, dialkylamino, alkoxy; and wherein the $R^3$ group can be in the ribosyl ("down" with respect to the sugar moiety when orienting the ring such that the oxygen is in the back) or the arabinosyl ("up") conformation;
B represents the boron moiety of a carboranyl group, and specifically includes anionic o-nido-7,8-$C_2B_9H_{(11\ or\ 12)}$ and neutral o-closo-1,2-$C_2B_{10}H_{12}$;
W is O, S, or Se;
X is O, S, S(O), S(O)$_2$, CH$_2$, CHOH, CHN$_3$ or NH;
Y is OH, SH, SeH, or halogen, and in particular, fluorine;
n is 1–5; and
m is 0 or 1.

4. A method for conducting boron neutron capture therapy, comprising administering to a patient in need thereof an effective amount of a compound selected from the group consisting of the following:

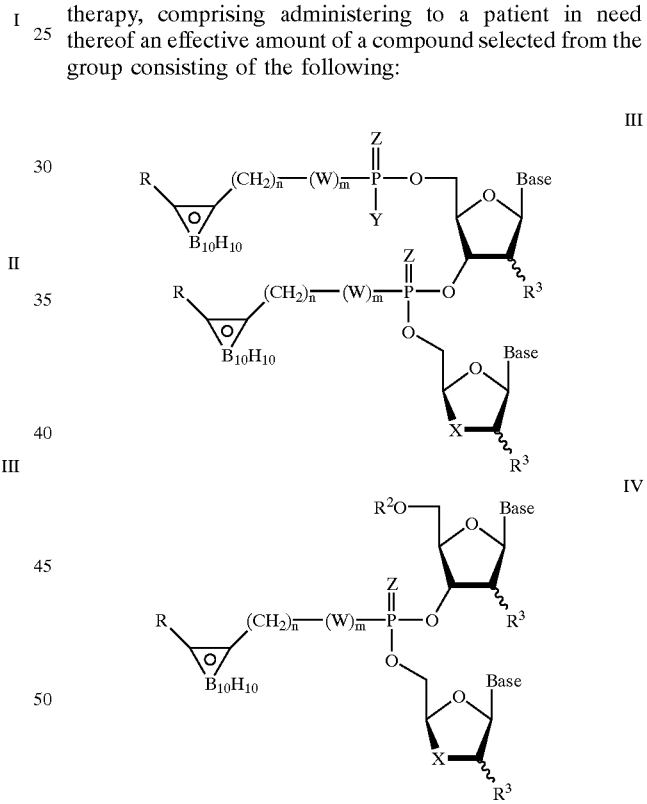

wherein: $R^1$, $R^2$, $R^3$, B, W, X, Y, Z, m and n are as defined in claim 3.

* * * * *